United States Patent
Yamamoto et al.

(10) Patent No.: US 11,998,396 B2
(45) Date of Patent: *Jun. 4, 2024

(54) ULTRASOUND DIAGNOSTIC APPARATUS AND OPERATION METHOD OF ULTRASOUND DIAGNOSTIC APPARATUS

(71) Applicant: FUJIFILM Corporation, Tokyo (JP)

(72) Inventors: Katsuya Yamamoto, Ashigarakami-gun (JP); Yasuhiko Morimoto, Ashigarakami-gun (JP); Satoru Okada, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/902,557

(22) Filed: Sep. 2, 2022

(65) Prior Publication Data

US 2023/0000471 A1    Jan. 5, 2023

Related U.S. Application Data

(63) Continuation of application No. 16/419,572, filed on May 22, 2019, now Pat. No. 11,471,132.

(30) Foreign Application Priority Data

Jun. 29, 2018   (JP) .................. 2018-124377

(51) Int. Cl.
*A61B 8/00*    (2006.01)
*A61B 8/12*    (2006.01)
(Continued)

(52) U.S. Cl.
CPC ............... *A61B 8/546* (2013.01); *A61B 8/12* (2013.01); *A61B 8/445* (2013.01); *B06B 1/0215* (2013.01);
(Continued)

(58) Field of Classification Search
CPC .......... A61B 8/546; A61B 8/12; A61B 8/445; A61B 8/4444; A61B 8/4483; A61B 8/463;
(Continued)

(56) References Cited

U.S. PATENT DOCUMENTS

2009/0287086 A1    11/2009  Hyuga
2012/0319529 A1    12/2012  Nakazawa et al.
(Continued)

FOREIGN PATENT DOCUMENTS

EP    1897498 A1    3/2008
JP    2006-255014 A    9/2006
(Continued)

OTHER PUBLICATIONS

European Communication pursuant to Article 94(3) EPC for European Application No. 19174178.4, dated Nov. 16, 2021.
(Continued)

*Primary Examiner* — Rochelle D Turchen
(74) *Attorney, Agent, or Firm* — Birch, Stewart, Kolasch & Birch, LLP

(57) ABSTRACT

An operation method of an ultrasound diagnostic apparatus includes executing one or more imaging series of steps with an ultrasound transducer; and applying a polarization processing to the ultrasound transducer one or more of before, after, and interleaved between the one or more imaging series of steps, where the polarization processing is separate from the one or more imaging series of steps.

15 Claims, 20 Drawing Sheets

(51) Int. Cl.
  *B06B 1/02* (2006.01)
  *B06B 1/06* (2006.01)
(52) U.S. Cl.
  CPC ........ *B06B 1/0607* (2013.01); *B06B 2201/76* (2013.01)
(58) Field of Classification Search
  CPC .. B06B 1/0215; B06B 1/0607; B06B 2201/55
  See application file for complete search history.

(56) References Cited

U.S. PATENT DOCUMENTS

| 2012/0323514 | A1 | 12/2012 | Nakazawa et al. |
| 2014/0066779 | A1 | 3/2014 | Nakanishi |
| 2015/0080727 | A1 | 3/2015 | Specht et al. |
| 2020/0025897 | A1* | 1/2020 | Borot ................. G01S 7/52046 |

FOREIGN PATENT DOCUMENTS

| JP | 2009-273838 A | 11/2009 |
| JP | 2013-005137 A | 1/2013 |
| JP | 2014-46062 A | 3/2014 |
| JP | 5874208 B2 | 3/2016 |
| JP | 6158017 B2 | 7/2017 |
| JP | 2017-143353 A | 8/2017 |

OTHER PUBLICATIONS

Extended European Search Report, dated Oct. 31, 2019, for European Application No. 19174178.4.
Japanese Notice of Reasons for Refusal for Japanese Application No. 2018-124377, dated Apr. 12, 2022, with an English translation.
U.S. Office Action for U.S. Appl. No. 16/419,572, dated Feb. 14, 2022 (Non-Final Office Action).
U.S. Office Action for U.S. Appl. No. 16/419,572, dated Jun. 23, 2022 (Notice of Allowance).
Japanese Notice of Reasons for Refusal for Japanese Application No. 2022-142863, dated May 9, 2023, with an English translation.
Extended European Search Report for corresponding European Application No. 23208517.5, dated Jan. 25, 2024.

* cited by examiner

FIG. 20
FIRST DISPLAY MODE
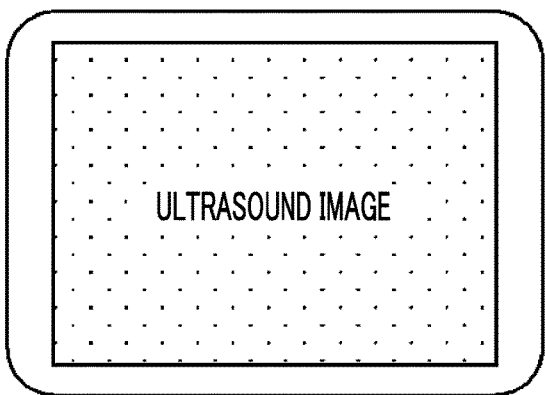
SECOND DISPLAY MODE
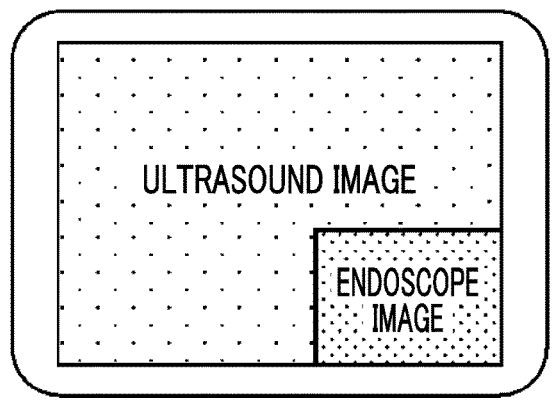
THIRD DISPLAY MODE
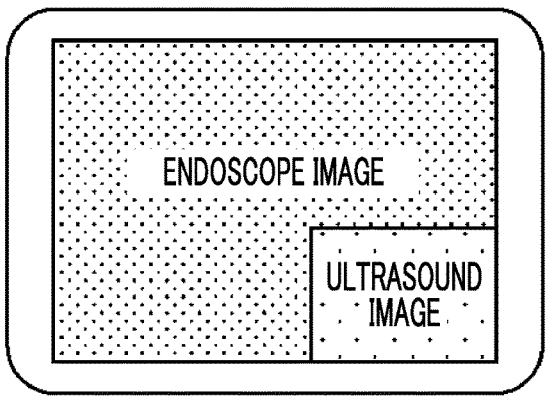
FOURTH DISPLAY MODE
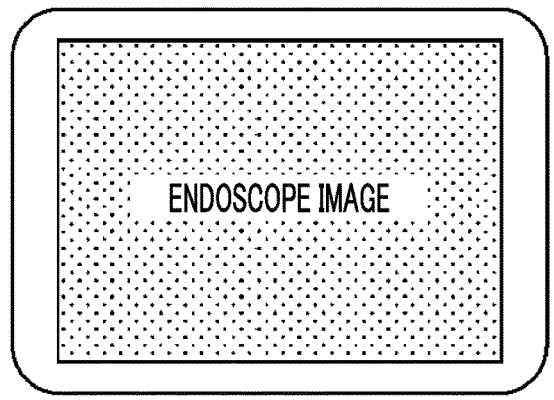

ULTRASOUND DIAGNOSTIC APPARATUS AND OPERATION METHOD OF ULTRASOUND DIAGNOSTIC APPARATUS

CROSS-REFERENCE TO RELATED APPLICATIONS

This application is a Continuation of application Ser. No. 16/419,572 filed on May 22, 2019, which claims priority under 35 U.S.C. § 119 to Japanese Patent Application No. 2018-124377, filed on Jun. 29, 2018. Each of the above application(s) is hereby expressly incorporated by reference, in its entirety, into the present application.

BACKGROUND OF THE INVENTION

1. Field of the Invention

The present invention relates to an ultrasound diagnostic apparatus, which performs polarization processing on a plurality of ultrasound transducers that an ultrasound endoscope comprises, and an operation method of an ultrasound diagnostic apparatus.

2. Description of the Related Art

As an ultrasound diagnostic apparatus for the purpose of biliary-pancreatic observation using the transgastrointestinal tract, an ultrasound endoscope in which an ultrasound observation portion is provided at the distal end portion of an endoscope is used. Such an ultrasound diagnostic apparatus acquires an ultrasound image of the inside of a body cavity of a subject by transmitting and receiving ultrasound waves by driving a plurality of ultrasound transducers inside the body cavity of the subject. In the ultrasound diagnostic apparatus, it is necessary to avoid a reduction in sensitivity in a state in which the ultrasound diagnostic apparatus is placed inside the body cavity of the subject.

In the ultrasound diagnostic apparatus, the plurality of ultrasound transducers are, for example, single crystal transducers that are piezoelectric elements, and are usually used in a polarized state. The ultrasound transducer that is a single crystal transducer can receive ultrasound waves with high sensitivity, but a depolarization phenomenon in which the degree of polarization decreases as the driving time increases may occur. In a case where a depolarization phenomenon occurs, the reception sensitivity of the ultrasound transducer decreases, which may affect the image quality of the ultrasound image. For this reason, as a measure against depolarization of the single crystal transducer, restoring the sensitivity by performing repolarization processing (hereinafter, also simply referred to as polarization processing) is also known.

The risk of depolarization is correlated with the thickness of the transducer, that is, the resonance frequency of the transducer. The risk decreases as the thickness of the transducer increases (as the frequency of the transducer decreases). For this reason, the risk of depolarization is avoided by using a transducer using a single crystal transducer for body surface in a low frequency band of 1 MHz to 6 MHz (refer to JP2013-005137A (JP5874208B)).

On the other hand, in the case of transmitting and receiving ultrasound waves by driving each ultrasound transducer inside the body cavity of the subject, since it is necessary to set the frequency of the ultrasound wave to a high frequency band of 7 MHz to 8 MHz level, a transducer having a relatively small thickness is used. However, as the thickness of the transducer decreases, the risk of occurrence of a depolarization phenomenon increases. Therefore, in the case of a thin transducer, a process of repolarization is required (refer to JP2017-143353A and JP6158017B).

For this reason, techniques for countermeasures against depolarization in the ultrasound diagnostic apparatus have been developed so far. For example, an ultrasound sensor as a piezoelectric sensor apparatus described in JP2013-005137A (JP5874208B) has a piezoelectric element having a piezoelectric body and a pair of electrodes interposing the piezoelectric body therebetween, a detection circuit for performing detection processing for detecting a detection signal output from the piezoelectric element, and a dedicated polarization processing circuit for performing polarization processing by applying a polarization voltage to the piezoelectric element. In the ultrasound sensor described in JP2013-005137A (JP5874208B) having such a configuration, it is possible to restore polarization by detecting depolarization from a difference in characteristics between the piezoelectric elements using the detection circuit and performing polarization processing using the dedicated polarization processing circuit. The polarization processing is performed at a timing at which the electric power is supplied, a timing at which a request signal for executing detection processing is input (each reception timing), or a timing at which a predetermined standby transition time has passed after the end of detection processing, for example. Therefore, even in a case where a depolarization phenomenon occurs in the piezoelectric element, the piezoelectric element can be polarized again. As a result, it is possible to maintain the reception sensitivity of the piezoelectric element.

As another example, the ultrasound sensor described in JP2017-143353A has a piezoelectric element and a driving circuit for driving the piezoelectric element. The driving circuit drives the piezoelectric element with a driving waveform having a first step of maintaining the polarization of the piezoelectric element with a first potential V1, a second step of transmitting an ultrasound wave to the piezoelectric element by applying a maximum potential VH and a minimum potential VL at least once, a third step of causing the piezoelectric element to stand by at a second potential V2, a fourth step of increasing the second potential V2 to a third potential V3, a fifth step of maintaining the third potential V3 while the piezoelectric element receives an ultrasound wave, and a sixth step of returning the third potential V3 to the first potential V1. In the ultrasound diagnostic apparatus described in JP2017-143353A having such a configuration, it is possible to drive the piezoelectric element while maintaining the polarization of the piezoelectric element by driving the piezoelectric element with the driving waveform having the above-described six steps. That is, JP2017-143353A describes that depolarization is prevented by studying the waveform for driving the piezoelectric element.

The ultrasound apparatus described in JP6158017B has an ultrasound transducer for transmitting and receiving ultrasound waves to and from a subject and a transmission and reception circuit comprising a power supply circuit, a transmission pulse output unit, a heating pulse output unit, a polarization voltage output unit, a reception beam former, and a polarization controller, or an integrated circuit further comprising a temperature detection unit in addition to the transmission and reception circuit.

In the ultrasound apparatus described in JP6158017B, the heating pulse output unit and the polarization voltage output unit are provided separately from the transmission pulse output unit. By outputting the polarization voltage of a necessary DC voltage from the polarization voltage output unit to the ultrasound transducer in a state in which the heating pulse from the heating pulse output unit is output to the ultrasound transducer to heat the ultrasound transducer, the ultrasound transducer is polarized. The technique described in JP6158017B can make the polarization voltage, which is higher than the voltage of the transmission pulse output from the transmission pulse output unit to the ultrasound transducer in order to transmit an ultrasound wave at the room temperature, lower than that at the room temperature by heating the ultrasound transducer.

SUMMARY OF THE INVENTION

As described above, in the ultrasound sensor and the ultrasound apparatus described in JP2013-005137A (JP5874208B), JP2017-143353A, and JP6158017B, it is possible to restore or maintain the polarization of the ultrasound transducer and the piezoelectric element formed of a piezoelectric body.

However, as in the ultrasound sensor described in JP2013-005137A (JP5874208B), providing a dedicated circuit for performing repolarization, a depolarization detection mechanism, and the like is a large hardware change factor. Accordingly, there is a problem that it is very difficult to mount those described above in the existing system.

In the ultrasound sensor described in JP2017-143353A, in order to prevent depolarization and maintain polarization, the pulse length of the driving waveform is increased by inserting a DC component into each driving waveform. Accordingly, there is a problem that the frame rate is reduced to affect the image quality of the ultrasound image. In addition, in order to prevent depolarization using such a driving waveform, there is a problem that there is a tradeoff between the image quality and the risk of depolarization.

In the ultrasound apparatus described in JP6158017B, repolarization can be performed only by the ultrasound apparatus. However, since a transmission pulse, a heating pulse, and a polarization voltage that is a DC voltage are output by the same integrated circuit or the same transmission and reception circuit, there is a problem that the circuit size increases to cause a cost increase.

In addition, in the ultrasound apparatus described in JP6158017B, it is necessary to heat the ultrasound transducer. However, in a case where this is applied to an ultrasound endoscope used within the body cavity of the subject, there is a problem that heating during the endoscope examination causes an increase in the temperature of a distal end of a probe, which is not preferable.

It is an object of the invention to provide an ultrasound diagnostic apparatus and an operation method of an ultrasound diagnostic apparatus capable of performing polarization processing of ultrasound transducers using an existing transmission circuit for transmitting a transmission signal to ultrasound transducers of an ultrasound endoscope, in a non-diagnosis time different from a time for acquiring an ultrasound image, without affecting the image quality of the ultrasound image and without causing a significant change in the circuit configuration and an increase in the circuit size by solving the aforementioned problems in the related art.

In order to achieve the aforementioned object, an ultrasound diagnostic apparatus according to a first aspect of the invention is an ultrasound diagnostic apparatus acquiring an ultrasound image and an endoscope image. The ultrasound diagnostic apparatus comprises: an ultrasound endoscope comprising an ultrasound observation portion that transmits ultrasound waves using an ultrasound transducer array, in which a plurality of ultrasound transducers are arranged, and receives reflected waves of the ultrasound waves; and an ultrasound processor apparatus comprising a transmission circuit that transmits a transmission signal to the plurality of ultrasound transducers in order to generate the ultrasound waves from the plurality of ultrasound transducers, a reception circuit that outputs a reception signal based on the reflected waves received by the plurality of ultrasound transducers, and an ultrasound image generation unit that generates the ultrasound image by converting the reception signal into an image in order to acquire the ultrasound image. The ultrasound processor apparatus further comprises a control circuit that performs transmission of the ultrasound waves and reception of the reflected waves within a diagnosis period for acquiring the ultrasound image and that performs polarization processing on the plurality of ultrasound transducers using the transmission circuit in a non-diagnosis period during which transmission of the ultrasound waves and reception of the reflected waves by the plurality of ultrasound transducers are not performed. The control circuit controls the transmission circuit to generate the transmission signal, which includes a diagnostic driving pulse applied to each of the plurality of ultrasound transducers that generate the ultrasound waves for acquiring the ultrasound image, in a case of acquiring the ultrasound image, controls the transmission circuit to generate a polarization driving pulse, which has a polarization driving voltage different from voltage of the diagnostic driving pulse within the same settable voltage range as the diagnostic driving pulse and has a frequency different from a probe frequency band for acquiring the ultrasound image, in order to perform the polarization processing of the plurality of ultrasound transducers in a case of performing the polarization processing, and applies the polarization driving pulse to the plurality of ultrasound transducers to perform the polarization processing of the plurality of ultrasound transducers with the polarization driving pulse.

Here, it is preferable that the control circuit controls the transmission circuit such that the probe frequency band and a frequency band of a main lobe of a driving waveform of the polarization driving pulse for driving the plurality of ultrasound transducers at the time of performing the polarization processing do not overlap each other at a sensitivity level of −20 dB or more.

It is preferable that the frequency band of the main lobe of the driving waveform of the polarization driving pulse is lower than the probe frequency band.

It is preferable that sensitivities of one or more side lobes generated within the probe frequency band with respect to the main lobe of the driving waveform of the polarization driving pulse are all 10 dB or less and that an average of the sensitivities of the one or more side lobes is −20 dB or less.

It is preferable that the driving waveform of the polarization driving pulse is a unipolar waveform.

It is preferable that the transmission circuit outputs a plurality of unipolar waveforms as the polarization driving pulse with a time of the minimum number of clocks defined in the transmission circuit as an interval between the unipolar waveforms.

It is preferable that the plurality of ultrasound transducers are single crystal transducers.

It is preferable that an image driving voltage of the diagnostic driving pulse and the polarization driving voltage of the polarization driving pulse have the same settable voltage range and that the transmission circuit uses the image driving voltage and the polarization driving voltage so as to be switched therebetween.

In addition, in order to achieve the aforementioned object, an operation method of an ultrasound diagnostic apparatus according to a second aspect of the invention is an operation method of an ultrasound diagnostic apparatus acquiring an ultrasound image and an endoscope image. The ultrasound diagnostic apparatus comprises: an ultrasound endoscope comprising an ultrasound observation portion having an ultrasound transducer array in which a plurality of ultrasound transducers are arranged; and an ultrasound processor apparatus having a transmission circuit that transmits a transmission signal to the plurality of ultrasound transducers, a reception circuit that outputs a reception signal based on reflected waves received by the plurality of ultrasound transducers, and an ultrasound image generation unit that generates the ultrasound image by converting the reception signal into an image. The operation method of an ultrasound diagnostic apparatus comprises: within a diagnosis period for acquiring the ultrasound image, a step in which the transmission circuit is controlled so as to generate the transmission signal, which includes a diagnostic driving pulse applied to each of the plurality of ultrasound transducers that generate ultrasound waves for acquiring the ultrasound image; a step in which the transmission signal generated from the transmission circuit is transmitted to the plurality of ultrasound transducers and the diagnostic driving pulse is applied to the plurality of ultrasound transducers to generate the ultrasound waves; a step in which the reflected waves of the ultrasound waves are received by the plurality of ultrasound transducers; a step of outputting a reception signal based on the reflected waves received from the reception circuit by the plurality of ultrasound transducers; and a step in which the ultrasound image generation unit receives the reception signal and converts the reception signal into an image to generate the ultrasound image, and in a non-diagnosis period during which transmission of the ultrasound waves and reception of the reflected waves by the plurality of ultrasound transducers are not performed, in order to perform polarization processing of the plurality of ultrasound transducers, a step in which the transmission circuit is controlled so as to generate a polarization driving pulse that has a polarization driving voltage different from voltage of the diagnostic driving pulse within the same settable voltage range as the diagnostic driving pulse and has a frequency different from a probe frequency band for acquiring the ultrasound image; and a step of applying the polarization driving pulse to the plurality of ultrasound transducers to perform the polarization processing of the plurality of ultrasound transducers with the polarization driving pulse.

Here, it is preferable that, in the step in which the transmission circuit is controlled so as to generate the transmission signal including the diagnostic driving pulse, the transmission circuit is controlled such that the probe frequency band and a frequency band of a main lobe of a driving waveform of the polarization driving pulse for driving the plurality of ultrasound transducers at the time of performing the polarization processing do not overlap each other at a sensitivity level of −20 dB or more.

It is preferable that the frequency band of the main lobe of the driving waveform of the polarization driving pulse is lower than the probe frequency band.

It is preferable that sensitivities of one or more side lobes generated within the probe frequency band with respect to the main lobe of the driving waveform of the polarization driving pulse are all 10 dB or less and that an average of the sensitivities of the one or more side lobes is −20 dB or less.

It is preferable that the driving waveform of the polarization driving pulse is a unipolar waveform.

It is preferable that, in the step in which the transmission circuit is controlled so as to generate the polarization driving pulse, the transmission circuit is controlled so as to output a plurality of unipolar waveforms as the polarization driving pulse with a time of the minimum number of clocks defined in the transmission circuit as an interval between the unipolar waveforms.

It is preferable that the plurality of ultrasound transducers are single crystal transducers.

It is preferable that an image driving voltage of the diagnostic driving pulse and the polarization driving voltage of the polarization driving pulse have the same settable voltage range and that the transmission circuit uses the image driving voltage and the polarization driving voltage so as to be switched therebetween.

According to the invention, the polarization processing of a plurality of ultrasound transducers is performed in a non-diagnosis time different from the time for acquiring an ultrasound image. Therefore, since the reception sensitivities of the plurality of ultrasound transducers can always be kept satisfactory without reducing the image quality of the ultrasound image, a high-quality ultrasound image can always be acquired without affecting the image quality of the ultrasound image.

In addition, according to the invention, the polarization processing of a plurality of ultrasound transducers is performed using the existing transmission circuit for transmitting the transmission signal to the ultrasound transducers of the ultrasound endoscope. Therefore, it is possible to perform the polarization processing of the ultrasound transducers without significantly changing the existing circuit configuration and without causing an increase in the circuit size.

According to the invention, even in a case where a single crystal transducer is adopted, it is possible to provide an ultrasound diagnostic apparatus having a highly sensitive ultrasound endoscope capable of performing repolarization with a waveform optimal for the polarization and to provide an operation method of an ultrasound diagnostic apparatus capable of performing repolarization with respect to polarization of the single crystal transducer with an optimal waveform in the highly sensitive ultrasound endoscope.

BRIEF DESCRIPTION OF THE DRAWINGS

FIG. 20 is a conceptual diagram of an example showing display modes.

DESCRIPTION OF THE PREFERRED EMBODIMENTS

An ultrasound diagnostic apparatus according to an embodiment of the invention will be described in detail below based on preferred embodiments shown in the accompanying diagrams. The present embodiment is a representative embodiment of the invention, but is merely an example and does not limit the invention. In addition, in this specification, the numerical range expressed by using "~" means a range including numerical values described before and after "~" as a lower limit and an upper limit.

<<Outline of Ultrasound Diagnostic Apparatus>>

Figure 1:
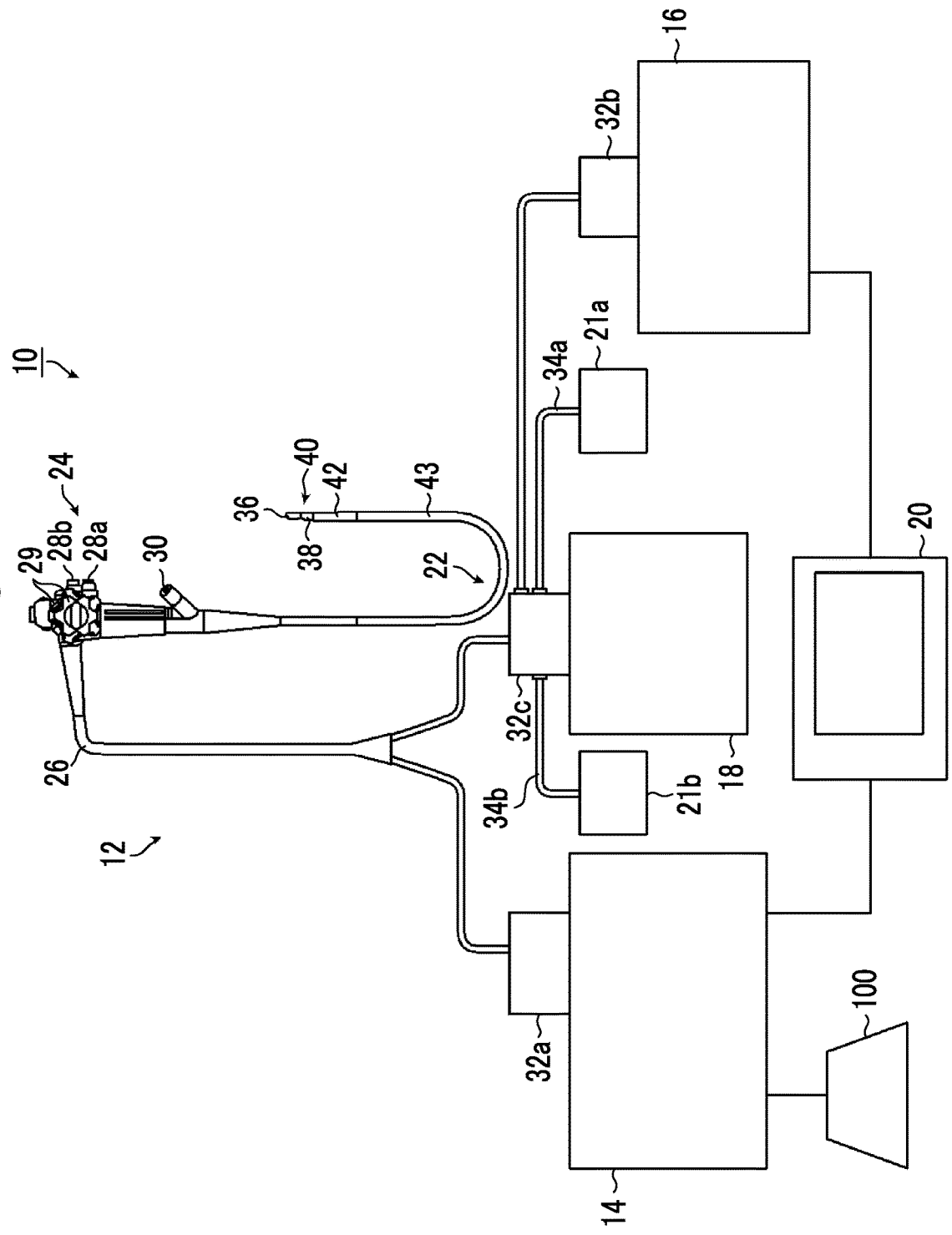
FIG. 1 is a diagram showing the schematic configuration of an ultrasound diagnostic apparatus according to an embodiment of the invention.

The outline of an ultrasound diagnostic apparatus 10 according to the present embodiment will be described with reference to FIG. 1. FIG. 1 is a diagram showing the schematic configuration of ultrasound diagnostic apparatus 10.

The ultrasound diagnostic apparatus 10 is used to observe (hereinafter, also referred to as ultrasound diagnosis) the state of an observation target part in a body of a patient, who is a subject, using ultrasound waves. Here, the observation target part is a part that is difficult to examine from the body surface side of the patient, for example, a gallbladder or a pancreas. By using the ultrasound diagnostic apparatus 10, it is possible to perform ultrasound diagnosis of the state of the observation target part and the presence or absence of an abnormality through gastrointestinal tracts such as esophagus, stomach, duodenum, small intestine, and large intestine which are body cavities of the patient.

The ultrasound diagnostic apparatus 10 acquires an ultrasound image and an endoscope image, and as shown in FIG. 1, has an ultrasound endoscope 12, an ultrasound processor apparatus 14, an endoscope processor apparatus 16, a light source device 18, a monitor 20, a water supply tank 21a, a suction pump 21b, and a console 100.

Figure 2:
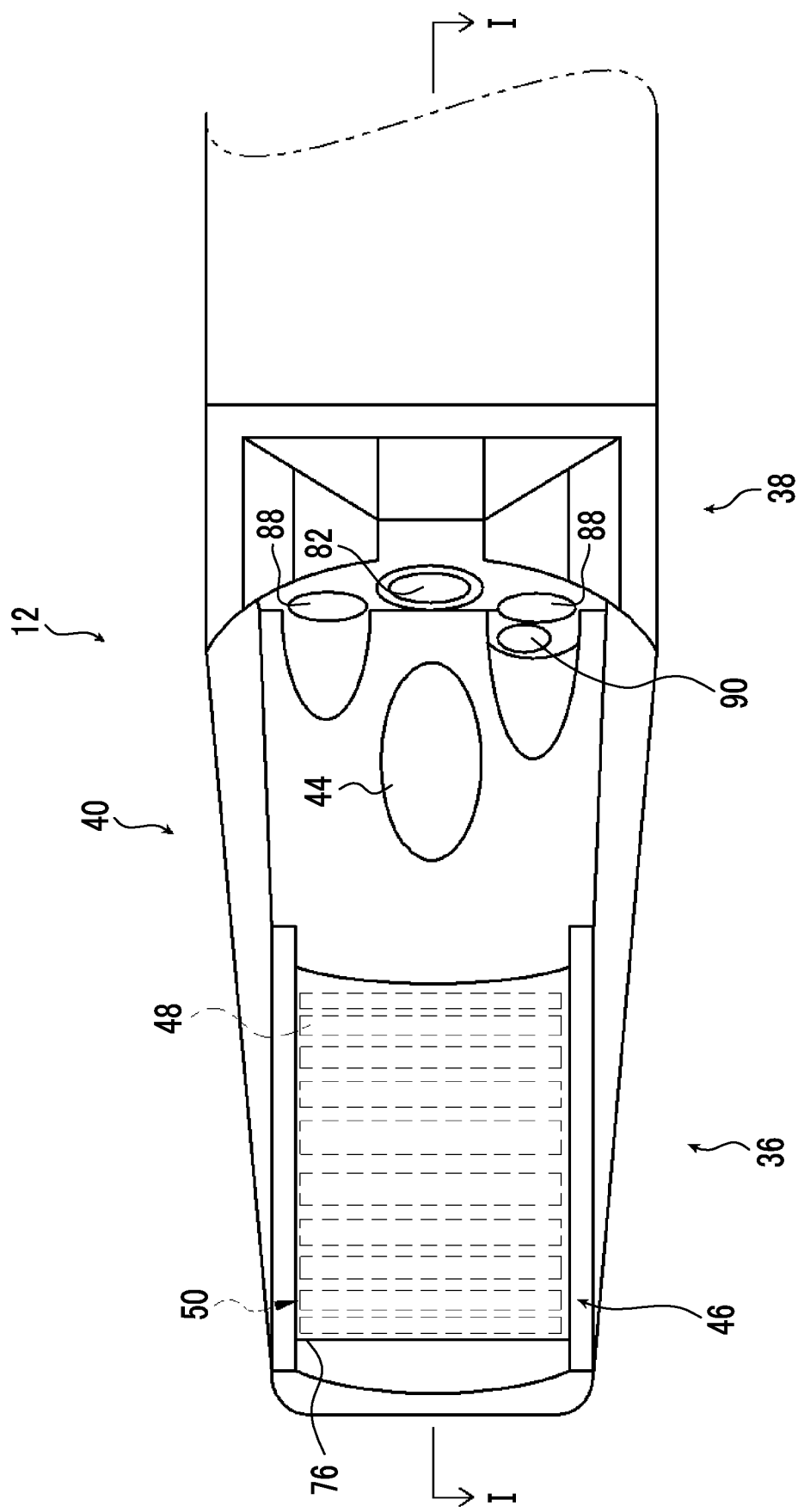
FIG. 2 is a plan view showing a distal end portion of an insertion part of an ultrasound endoscope and its periphery shown in FIG. 1.
Figure 3:
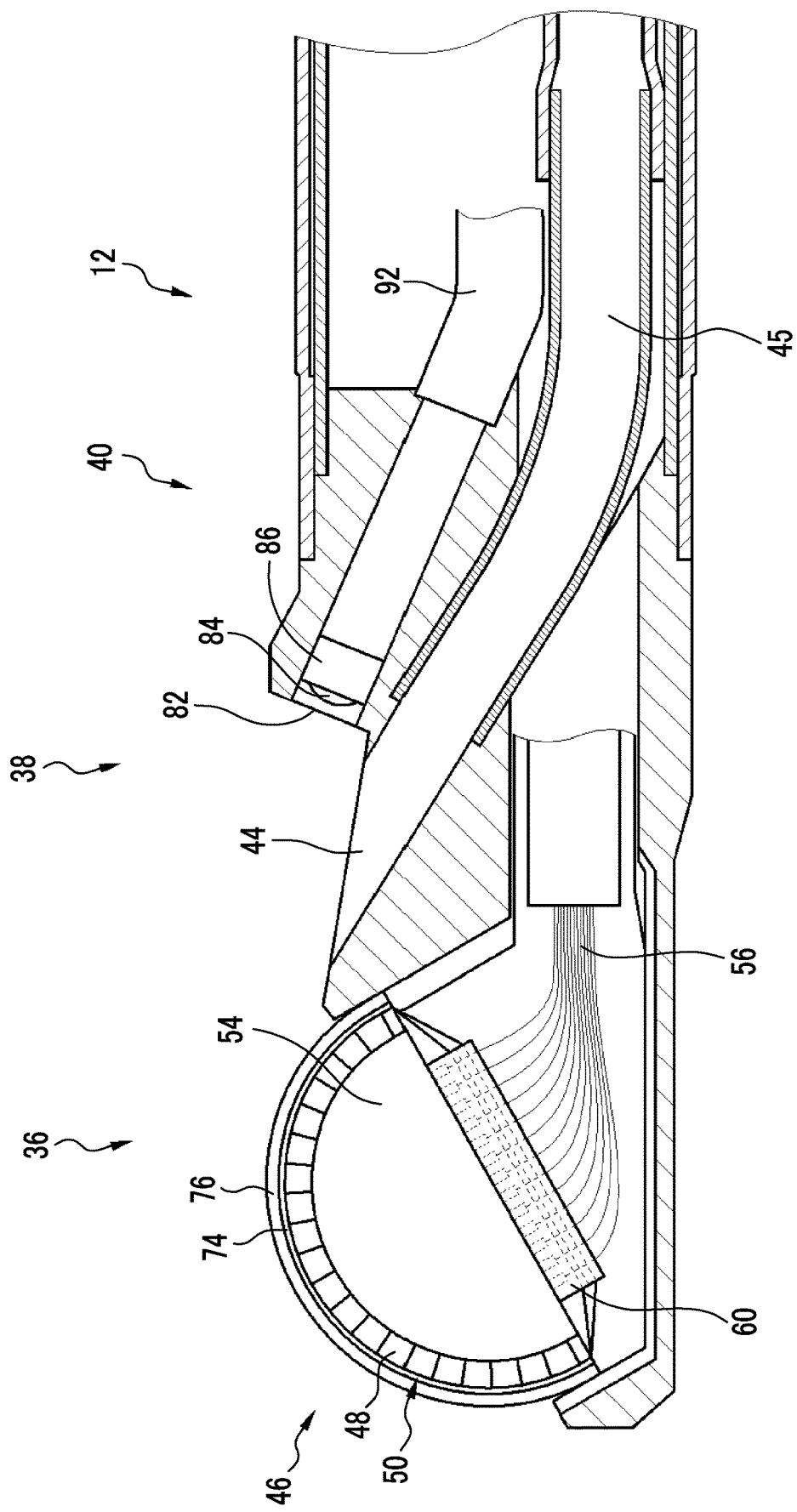
FIG. 3 is a diagram showing a cross section of the distal end portion of the insertion part of the ultrasound endoscope shown in FIG. 2 taken along the line I-I in FIG. 2.

The ultrasound endoscope 12 is an endoscope, and comprises an insertion part 22 to be inserted into the body cavity of a patient, an operation unit 24 operated by an operator (user), such as a doctor or a technician, and an ultrasound transducer unit 46 attached to a distal end portion 40 of the insertion part 22 (refer to FIGS. 2 and 3). By the function of the ultrasound endoscope 12, the operator can acquire an endoscope image of the inner wall of the body cavity of the patient and an ultrasound image of the observation target part.

Here, the "endoscope image" is an image obtained by imaging the inner wall of the body cavity of the patient using an optical method. The "ultrasound image" is an image obtained by receiving a reflected wave (echo) of an ultrasound wave transmitted from the inside of the body cavity of the patient to the observation target part and converting the reception signal into an image. The ultrasound endoscope 12 will be described in detail later.

The ultrasound processor apparatus 14 is connected to the ultrasound endoscope 12 through a universal cord 26 and an ultrasound connector 32a provided at an end portion of the universal cord 26. The ultrasound processor apparatus 14 controls the ultrasound transducer unit 46 of the ultrasound endoscope 12 to transmit the ultrasound wave. In addition, the ultrasound processor apparatus 14 generates an ultrasound image by converting the reception signal in a case where the reflected wave (echo) of the transmitted ultrasound wave is received by the ultrasound transducer unit 46 into an image.

The ultrasound processor apparatus 14 will be described in detail later.

The endoscope processor apparatus 16 is connected to the ultrasound endoscope 12 through the universal cord 26 and an endoscope connector 32b provided at an end portion of the universal cord 26. The endoscope processor apparatus 16 generates an endoscope image by acquiring image data of an observation target adjacent part imaged by the ultrasound endoscope 12 (more specifically, a solid-state imaging element 86 to be described later) and performing predetermined image processing on the acquired image data.

Here, the "observation target adjacent part" is a portion of the inner wall of the body cavity of the patient that is adjacent to the observation target part.

In the present embodiment, the ultrasound processor apparatus 14 and the endoscope processor apparatus 16 are formed by two apparatuses (computers) provided separately. However, the invention is not limited thereto, and both the ultrasound processor apparatus 14 and the endoscope processor apparatus 16 may be formed by one apparatus.

The light source device 18 is connected to the ultrasound endoscope 12 through the universal cord 26 and a light source connector 32c provided at an end portion of the universal cord 26. The light source device 18 emits white light or specific wavelength light formed of three primary color light components of red light, green light, and blue light at the time of imaging the observation target adjacent part using the ultrasound endoscope 12. The light emitted from the light source device 18 propagates through the ultrasound endoscope 12 through a light guide (not shown) included in the universal cord 26, and is emitted from the ultrasound endoscope 12 (more specifically, an illumination window 88 to be described later). As a result, the observation target adjacent part is illuminated with the light from the light source device 18.

The monitor 20 is connected to the ultrasound processor apparatus 14, and the endoscope processor apparatus 16, and displays an ultrasound image generated by the ultrasound processor apparatus 14 and an endoscope image generated by the endoscope processor apparatus 16. As a display method of the ultrasound image and the endoscope image, either one of the images may be switched and displayed on the monitor 20, or both the images may be displayed at the same time. Display modes of the ultrasound image and the endoscope image will be described later.

In the present embodiment, the ultrasound image and the endoscope image are displayed on one monitor 20. However, a monitor for displaying the ultrasound image and a monitor for displaying the endoscope image may be separately provided. In addition, the ultrasound image and the endoscope image may be displayed in a display form other than the monitor 20. For example, the ultrasound image and the endoscope image may be displayed on a display of a terminal carried by the operator.

The console 100 is an apparatus provided for the operator to input information necessary for ultrasound diagnosis or for the operator to instruct the ultrasound processor apparatus 14 to start ultrasound diagnosis. The console 100 is configured to include, for example, a keyboard, a mouse, a trackball, a touch pad, and a touch panel. In a case where the console 100 is operated, a CPU (control circuit) 152 (refer to FIG. 4) of the ultrasound processor apparatus 14 controls each unit of the apparatus (for example, a reception circuit 142 and a transmission circuit 144 to be described later) according to the operation content.

Specifically, the operator inputs examination information (for example, examination order information including a date, an order number, and the like and patient information including a patient ID, a patient name, and the like) through the console 100 before starting the ultrasound diagnosis. In a case where the operator gives an instruction to start the ultrasound diagnosis through the console 100 after the input of the examination information is completed, the CPU 152 of the ultrasound processor apparatus 14 controls each unit of the ultrasound processor apparatus 14 so that the ultrasound diagnosis is performed based on the input examination information.

The operator can set various control parameters with the console 100 at the time of performing the ultrasound diagnosis. As the control parameters, for example, selection results of a live mode and a freeze mode, set values of the display depth (depth), selection results of an ultrasound image generation mode, and the like can be mentioned.

Here, the "live mode" is a mode in which ultrasound images (moving images) obtained at a predetermined frame rate are sequentially displayed (displayed in real time). The "freeze mode" is a mode in which an image (still image) of one frame of an ultrasound image (moving image) generated in the past is read out from a cine memory 150 to be described later and displayed.

There are a plurality of ultrasound image generation modes that can be selected in the present embodiment. Specifically, there are a brightness (B) mode, a color flow (CF) mode, and a pulse wave (PW) mode. The B mode is a mode in which a tomographic image is displayed by converting the amplitude of the ultrasound echo into a brightness. The CF mode is a mode in which average blood flow speed, flow fluctuation, strength of flow signal, flow power, and the like are mapped to various colors and displayed so as to be superimposed on a B mode image. The PW mode is a mode in which the speed (for example, blood flow speed) of the ultrasound echo source detected based on the transmission and reception of the pulse wave is displayed.

The ultrasound image generation modes described above are merely examples, and modes other than the above-described three kinds of modes, for example, an amplitude (A) mode, a motion (M) mode, and a contrast mode may be further included, or a mode for acquiring a Doppler image may be included.

<<Configuration of Ultrasound Endoscope 12>>

Figure 4:
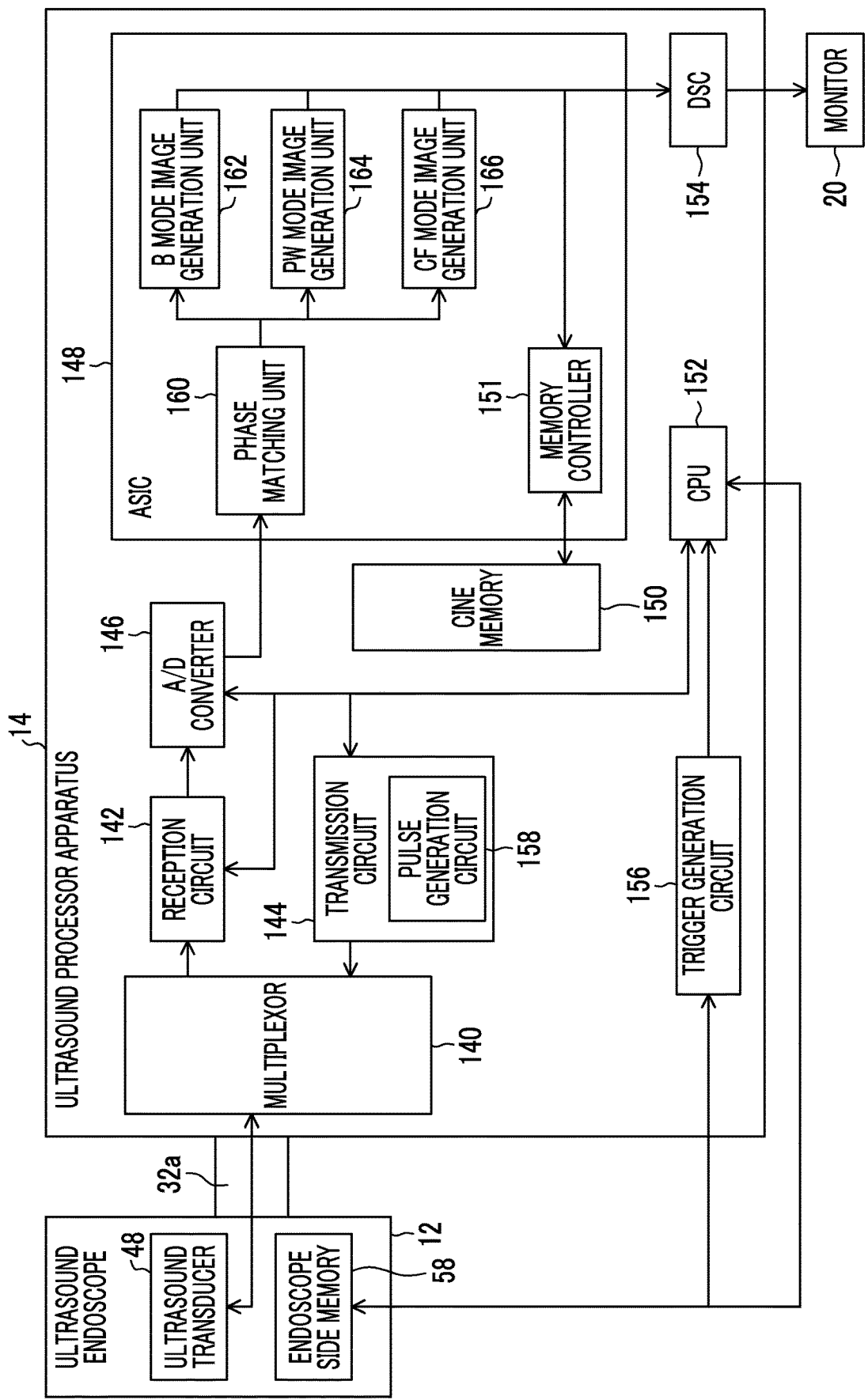
FIG. 4 is a block diagram showing the configuration of an ultrasound processor apparatus shown in FIG. 1.

Next, the configuration of the ultrasound endoscope 12 will be described with reference to FIGS. 1 to 4. FIG. 2 is an enlarged plan view showing a distal end portion of an insertion part 22 of an ultrasound endoscope 12 and the periphery thereof. FIG. 3 is a cross-sectional view showing a cross section of the distal end portion 40 of the insertion part 22 of the ultrasound endoscope 12 taken along the line I-I in FIG. 2. FIG. 4 is a block diagram showing the configuration of the ultrasound processor apparatus 14 shown in FIG. 1.

As described above the ultrasound endoscope 12 has the insertion part 22 and the operation unit 24. As shown in FIG. 1, the insertion part 22 comprises the distal end portion 40, a bending portion 42, and a flexible portion 43 in order from the distal end side (free end side). As shown in FIG. 2, an ultrasound observation portion 36 and an endoscope observation portion 38 are provided in the distal end portion 40. As shown in FIG. 3, the ultrasound transducer unit 46 comprising a plurality of ultrasound transducers 48 is disposed in the ultrasound observation portion 36.

As shown in FIG. 2, a treatment tool lead-out port 44 is provided in the distal end portion 40. The treatment tool lead-out port 44 serves as an outlet of a treatment tool (not shown), such as forceps, an insertion needle, or a high frequency scalpel. In addition, the treatment tool lead-out port 44 serves as a suction port in the case of sucking aspirates, such as blood and body waste.

The bending portion 42 is a portion continuously provided on the more proximal side (side opposite to the side where the ultrasound transducer unit 46 is provided) than the distal end portion 40, and can bend freely. The flexible portion 43 is a portion connecting the bending portion 42 and the operation unit 24 to each other, has flexibility, and is provided so as to extend in an elongated state.

A plurality of pipe lines for air and water supply and a plurality of pipe lines for suction are formed in the insertion part 22 and the operation unit 24, respectively. In addition, a treatment tool channel 45 whose one end communicates with the treatment tool lead-out port 44 is formed in each of the insertion part 22 and the operation unit 24.

Next, the ultrasound observation portion 36, the endoscope observation portion 38, the water supply tank 21a, the suction pump 21b, and the operation unit 24 among the components of the ultrasound endoscope 12 will be described in detail.

(Ultrasound Observation Portion)

The ultrasound observation portion 36 is a portion provided to acquire an ultrasound image, and is disposed on the distal end side in the distal end portion 40 of the insertion part 22. As shown in FIG. 3, the ultrasound observation portion 36 comprises the ultrasound transducer unit 46, a plurality of coaxial cables 56, and a flexible printed circuit (FPC) 60.

The ultrasound transducer unit 46 corresponds to an ultrasound probe (probe), and transmits an ultrasound wave using an ultrasound transducer array 50, in which a plurality of ultrasound transducers 48 to be described later are arranged, in the body cavity of the patient, receives a reflected wave (echo) of the ultrasound wave reflected by the observation target part, and outputs a reception signal. The ultrasound transducer unit 46 according to the present embodiment is a convex type, and transmits an ultrasound wave radially (in an arc shape). However, the type (model) of the ultrasound transducer unit 46 is not particularly limited, and other types may be used as long as it is possible to transmit and receive ultrasound waves. For example, a sector type, a linear type, and a radial type may be used.

As shown in FIG. 3, the ultrasound transducer unit 46 is formed by laminating a backing material layer 54, the ultrasound transducer array 50, an acoustic matching layer 74, and an acoustic lens 76.

The ultrasound transducer array 50 includes a plurality of ultrasound transducers 48 (ultrasound transducers) arranged in a one-dimensional array. More specifically, the ultrasound transducer array 50 is formed by arranging N (for example, N=128) ultrasound transducers 48 at equal intervals in a convex bending shape along the axial direction of the distal end portion 40 (longitudinal axis direction of the insertion part 22). The ultrasound transducer array 50 may be one in which a plurality of ultrasound transducers 48 are disposed in a two-dimensional array.

Each of the N ultrasound transducers 48 is formed by disposing electrodes on both surfaces of a single crystal transducer that is a piezoelectric element. As the single crystal transducer, any of quartz, lithium niobate, lead magnesium niobate (PMN), lead magnesium niobate-lead titanate (PMN-PT), lead zinc niobate (PZN), zinc niobate-lead titanate (PZN-PT), lead indium niobate (PIN), lead titanate (PT), lithium tantalate, langasite, and zinc oxide can be used.

The electrodes is an individual electrode (not shown) individually provided for each of the plurality of ultrasound transducers 48 and a transducer ground (not shown) common to the plurality of ultrasound transducers 48. In addition, the electrodes are electrically connected to the ultrasound processor apparatus 14 through the coaxial cable 56 and the FPC 60.

The ultrasound transducer 48 according to the present embodiment needs to be driven (vibrated) at a relatively high frequency of 7 MHz to 8 MHz level in order to acquire an ultrasound image in the body cavity of the patient. For this reason, the thickness of the piezoelectric element forming the ultrasound transducer 48 is designed to be relatively small. For example, the thickness of the piezoelectric element forming the ultrasound transducer 48 is 75 μm to 125 μm, preferably 90 μm to 110 μm.

A diagnostic driving pulse that is a pulsed driving voltage is supplied from the ultrasound processor apparatus 14 to each ultrasound transducer 48, as an input signal (transmission signal), through the coaxial cable 56. In a case where the driving voltage is applied to the electrodes of the ultrasound transducer 48, the piezoelectric element expands and contracts to drive (vibrate) the ultrasound transducer 48. As a result, a pulsed ultrasound wave is output from the ultrasound transducer 48. In this case, the amplitude of the ultrasound wave output from the ultrasound transducer 48 has a magnitude corresponding to the intensity (output intensity) in a case where the ultrasound transducer 48 outputs the ultrasound wave. Here, the output intensity is defined as the magnitude of the sound pressure of the ultrasound wave output from the ultrasound transducer 48.

Each ultrasound transducer 48 vibrates (is driven) upon receiving the reflected wave (echo) of the ultrasound wave, and the piezoelectric element of each ultrasound transducer 48 generates an electric signal. The electric signal is output from each ultrasound transducer 48 to the ultrasound processor apparatus 14 as a reception signal of the ultrasound wave. In this case, the magnitude (voltage value) of the electric signal output from the ultrasound transducer 48 has a magnitude corresponding to the reception sensitivity in a case where the ultrasound transducer 48 receives the ultrasound wave. Here, the reception sensitivity is defined as a ratio of the amplitude of the electric signal, which is output from the ultrasound transducer 48 in response to reception of the ultrasound wave, to the amplitude of the ultrasound wave transmitted by the ultrasound transducer 48.

In the present embodiment, by sequentially driving the N ultrasound transducers 48 with an electronic switch such as a multiplexer 140 (refer to FIG. 4), an ultrasound scan occurs in a scanning range along the curved surface on which the ultrasound transducer array 50 is disposed, for example, in the range of about several tens of mm from the center of curvature of the curved surface. More specifically, in the case of acquiring a B mode image (tomographic image) as an ultrasound image, a driving voltage is supplied to m (for example, m=N/2) ultrasound transducers 48 (hereinafter, referred to as driving target transducers) arranged in series, among the N ultrasound transducers 48, by opening channel selection of the multiplexer 140. As a result, the m driving target transducers are driven, and an ultrasound wave is output from each driving target transducer of the opening channel. The ultrasound waves output from the m driving target transducers are immediately synthesized, and the composite wave (ultrasound beam) is transmitted to the observation target part. Thereafter, each of the m driving target transducers receives an ultrasound wave (echo) reflected at the observation target part, and outputs an electric signal (reception signal) corresponding to the reception sensitivity at that point in time.

Then, the above-described series of steps (that is, supply of a driving voltage, transmission and reception of ultrasound waves, and output of an electric signal) are repeatedly performed while shifting the position of the driving target transducer, among the N ultrasound transducers 48, one by one (one ultrasound transducer 48 at a time). Specifically, the above-described series of steps are started from m driving target transducers on both sides of the ultrasound transducer 48 located at one end among the N ultrasound transducers 48. Then, the above-described series of steps are repeated each time the position of the driving target transducer is shifted due to switching of the opening channel by the multiplexer 140. Finally, the above-described series of steps are repeatedly performed a total of N times up to m driving target transducers on both sides of the ultrasound transducer 48 located at the other end among the N ultrasound transducers 48.

The backing material layer 54 supports each ultrasound transducer 48 of the ultrasound transducer array 50 from the back surface side. In addition, the backing material layer 54 has a function of attenuating ultrasound waves propagating to the backing material layer 54 side among ultrasound waves emitted from the ultrasound transducer 48 or ultrasound waves (echoes) reflected by the observation target part. The backing material is a material having rigidity, such as hard rubber, and an ultrasound damping material (ferrite, ceramics, and the like) is added as necessary.

The acoustic matching layer 74 is superimposed on the ultrasound transducer array 50, and is provided for acoustic impedance matching between the body of the patient and the ultrasound transducer 48. Since the acoustic matching layer 74 is provided, it is possible to increase the transmittance of the ultrasound wave. As a material of the acoustic matching layer 74, it is possible to use various organic materials whose acoustic impedance values are closer to impedance value of the human body of the patient than the piezoelectric element of the ultrasound transducer 48. Specific examples of the material of the acoustic matching layer 74 include epoxy resin, silicone rubber, polyimide, polyethylene, and the like.

The acoustic lens 76 superimposed on the acoustic matching layer 74 converges ultrasound waves emitted from the ultrasound transducer array 50 toward the observation target part. The acoustic lens 76 is formed of, for example, silicon resin (millable silicone rubber (HTV rubber), liquid silicone rubber (RTV rubber), and the like), butadiene resin, and polyurethane resin, and powders of titanium oxide, alumina, silica, and the like are mixed as necessary. The FPC 60 is electrically connected to the electrode of each ultrasound transducer 48. Each of the plurality of coaxial cables 56 is wired to the FPC 60 at one end thereof. Then, in a case where the ultrasound endoscope 12 is connected to the ultrasound processor apparatus 14 through the ultrasound connector 32a, each of the plurality of coaxial cables 56 is electrically connected to the ultrasound processor apparatus 14 at the other end (side opposite to the FPC 60).

In the present embodiment, the ultrasound endoscope 12 comprises an endoscope side memory 58 (refer to FIG. 4). The endoscope side memory 58 stores driving times of the plurality of ultrasound transducers 48 at the time of ultrasound diagnosis. Strictly speaking, in the endoscope side memory 58, the cumulative driving time of the driving target transducer among the plurality of ultrasound transducers 48 is stored.

In the present embodiment, an execution period of ultrasound diagnosis, that is, a period from the start of acquisition of an ultrasound image (moving image) to the end thereof (more specifically, a time during which ultrasound diagnosis is performed in the live mode), is set as the cumulative driving time. However, the invention is not limited thereto, and the time for which the driving voltage is supplied to the driving target transducer may be set as the cumulative driving time.

In a state in which the ultrasound endoscope 12 is connected to the ultrasound processor apparatus 14, the CPU 152 of the ultrasound processor apparatus 14 can access the endoscope side memory 58 to read the cumulative driving time stored in the endoscope side memory 58. In addition, the CPU 152 of the ultrasound processor apparatus 14 rewrites the cumulative driving time stored in the endoscope side memory 58 to a default value, or updates the stored cumulative driving time to a new cumulative driving time in a case where the cumulative driving time changes with the execution of ultrasound diagnosis.

(Endoscope Observation Portion)

The endoscope observation portion 38 is a portion provided to acquire an endoscope image, and is disposed on the more proximal side than ultrasound observation portion 36 in the distal end portion 40 of the insertion part 22. As shown in FIGS. 2 and 3, the endoscope observation portion 38 includes the observation window 82, an objective lens 84, the solid-state imaging element 86, the illumination window 88, the cleaning nozzle 90, a wiring cable 92, and the like.

The observation window 82 is attached so as to be inclined with respect to the axial direction (longitudinal axis direction of the insertion part 22) at the distal end portion 40 of the insertion part 22. Light incident through the observation window 82 and reflected at the observation target adjacent part is focused on the imaging surface of the solid-state imaging element 86 by the objective lens 84.

The solid-state imaging element 86 photoelectrically converts the reflected light of the observation target adjacent part, which is focused on the imaging surface after being transmitted through the observation window 82 and the objective lens 84, and outputs an imaging signal. As the solid-state imaging element 86, it is possible to use a charge coupled device (CCD), a complementary metal oxide semiconductor (CMOS), and the like. The captured image signal output from the solid-state imaging element 86 is transmitted to the endoscope processor apparatus 16 by the universal cord 26 through the wiring cable 92 extending from the insertion part 22 to the operation unit 24.

The illumination window 88 is provided at both side positions of the observation window 82. An exit end of a light guide (not shown) is connected to the illumination window 88. The light guide extends from the insertion part 22 to the operation unit 24, and its incidence end is connected to the light source device 18 connected through the universal cord 26. The illumination light emitted from the light source device 18 is transmitted through the light guide and is emitted from the illumination window 88 toward the observation target adjacent part.

The cleaning nozzle 90 is an ejection hole formed at the distal end portion 40 of the insertion part 22 in order to clean the surfaces of the observation window 82 and the illumination window 88. From the cleaning nozzle 90, air or cleaning liquid is ejected toward the observation window 82 and the illumination window 88. In the present embodiment, the cleaning liquid ejected from the cleaning nozzle 90 is water, in particular, degassed water. However, the cleaning liquid is not particularly limited, and other liquids, for example, normal water (water that is not degassed) may be used.

(Water Supply Tank and Suction Pump)

The water supply tank 21a is a tank that stores degassed water, and is connected to the light source connector 32c by an air and water supply tube 34a. Degassed water is used as a cleaning liquid ejected from the cleaning nozzle 90. The suction pump 21b sucks aspirates (including degassed water supplied for cleaning) inside the body cavity through the treatment tool lead-out port 44.

The suction pump 21b is connected to the light source connector 32c by a suction tube 34b. The ultrasound diagnostic apparatus 10 may comprise an air supply pump for supplying air to a predetermined air supply destination and the like.

In the insertion part 22 and the operation unit 24, the treatment tool channel 45 and an air and water supply pipe line (not shown) are provided.

The treatment tool channel 45 communicates between a treatment tool insertion port 30 and the treatment tool lead-out port 44 provided in the operation unit 24. The treatment tool channel 45 is connected to a suction button 28b provided in the operation unit 24. The suction button 28b is connected to the suction pump 21b in addition to the treatment tool channel 45.

The air and water supply pipe line communicates with the cleaning nozzle 90 at one end side, and is connected to an air and water supply button 28a provided in the operation unit 24 at the other end side. The air and water supply button 28a is connected to the water supply tank 21a in addition to the air and water supply pipe line.

(Operation Unit)

The operation unit 24 is a unit operated by the operator at the start of ultrasound diagnosis, during diagnosis, at the end of diagnostic, and one end of the universal cord 26 is connected to one end of the operation unit 24. As shown in FIG. 1, the operation unit 24 has the air and water supply button 28a, the suction button 28b, a pair of angle knobs 29, and a treatment tool insertion port (forceps port) 30.

In a case where each of the pair of angle knobs 29 is rotated, the bending portion 42 is remotely operated to be bent and deformed. By this deformation operation, the distal end portion 40 of the insertion part 22 in which the ultrasound observation portion 36 and the endoscope observation portion 38 are provided can be directed in a desired direction.

The treatment tool insertion port 30 is a hole formed to insert a treatment tool (not shown), such as forceps, and communicates with the treatment tool lead-out port 44 through the treatment tool channel 45. The treatment tool inserted into the treatment tool insertion port 30 is introduced into the body cavity from the treatment tool lead-out port 44 after passing through the treatment tool channel 45.

The air and water supply button 28a and the suction button 28b are two-stage switching type push buttons, and are operated to switch the opening and closing of the pipe line provided inside each of the insertion part 22 and the operation unit 24.

<<Configuration of Ultrasound Processor Apparatus>>

The ultrasound processor apparatus 14 causes the ultrasound transducer unit 46 to transmit and receive ultrasound waves, and generates an ultrasound image by converting the reception signal, which is output from the ultrasound transducer 48 (specifically, a driving target element) at the time of ultrasound wave reception, into an image. In addition, the ultrasound processor apparatus 14 displays the generated ultrasound image on the monitor 20.

In the present embodiment, the ultrasound processor apparatus 14 supplies a polarization voltage to a polarization target transducer, among the N ultrasound transducers 48, to polarize the polarization target transducer. By performing the polarization processing, the depolarized ultrasound transducer 48 can be polarized again by repeating the ultrasound diagnosis. As a result, it is possible to restore the reception sensitivity of the ultrasound transducer 48 with respect to ultrasound waves to a satisfactory level.

As shown in FIG. 4, the ultrasound processor apparatus 14 has the multiplexer 140, the reception circuit 142, the transmission circuit 144, an A/D converter 146, an application specific integrated circuit (ASIC) 148, the cine memory 150, a trigger generation circuit 156, a central processing unit (CPU) 152, and a digital scan converter (DSC) 154.

The reception circuit 142 and the transmission circuit 144 are electrically connected to the ultrasound transducer array 50 of the ultrasound endoscope 12. The multiplexer 140 selects a maximum of m driving target transducers from the N ultrasound transducers 48, and opens their channels.

The transmission circuit 144 is configured to include a field programmable gate array (FPGA), a pulser (pulse generation circuit 158), a switch (SW), and the like, and is connected to the multiplexer 140 (MUX). Instead of the FPGA, an application specific integrated circuit (ASIC) may be used.

The transmission circuit 144 is a circuit that supplies a driving voltage for ultrasound wave transmission to the driving target transducers selected by the multiplexer 140, according to the control signal transmitted from the CPU 152, in order to transmit ultrasound waves from the ultrasound transducer unit 46. The driving voltage is a pulsed voltage signal (transmission signal), and is applied to the electrodes of the driving target transducers through the universal cord 26 and the coaxial cable 56.

The transmission circuit 144 has a pulse generation circuit 158 that generates a transmission signal based on a control signal. Under the control of the CPU 152, a transmission signal for driving a plurality of ultrasound transducers 48 to generate ultrasound waves is generated using the pulse generation circuit 158, and the generated transmission signal is supplied to the plurality of ultrasound transducers 48.

In addition, under the control of the CPU 152, in the case of performing ultrasound diagnosis, the transmission circuit 144 generates a first transmission signal having a driving voltage for performing ultrasound diagnosis using the pulse generation circuit 158. In addition, under the control of the CPU 152, in the case of performing polarization processing, a second transmission signal having a polarization voltage for performing polarization processing is generated using the same pulse generation circuit 158 as in the case of generating the first transmission signal.

The reception circuit 142 is a circuit that receives an electric signal output from the driving target transducer that has received an ultrasound wave (echo), that is, a reception signal. In addition, according to the control signal transmitted from the CPU 152, the reception circuit 142 amplifies the reception signal received from the ultrasound transducer 48 and transmits the amplified signal to the A/D converter 146. The A/D converter 146 is connected to the reception circuit 142, and converts the reception signal received from the reception circuit 142 from an analog signal to a digital signal and outputs the converted digital signal to the ASIC 148.

The ASIC 148 is connected to the A/D converter 146. As shown in FIG. 4, the ASIC 148 forms a phase matching unit 160, a B mode image generation unit 162, a PW mode image generation unit 164, a CF mode image generation unit 166, and a memory controller 151.

In the present embodiment, the above-described functions (specifically, the phase matching unit 160, the B mode image generation unit 162, the PW mode image generation unit 164, the CF mode image generation unit 166, and the memory controller 151) are realized by a hardware circuit, such as the ASIC 148. However, the invention is not limited thereto. The above-described functions may be realized by making the central processing unit (CPU) and software (computer program) for executing various kinds of data processing cooperate with each other.

The phase matching unit 160 performs processing for phasing addition (addition after matching the phases of reception data) by giving a delay time to the reception signal (reception data) digitized by the A/D converter 146. By the phasing addition processing, a sound ray signal with narrowed focus of the ultrasound echo is generated.

The B mode image generation unit 162, the PW mode image generation unit 164, and the CF mode image generation unit 166 generate an ultrasound image based on the electric signal (strictly speaking, the sound ray signal generated by phasing and adding the reception data) that is output from the driving target transducer among the plurality of ultrasound transducers 48 in a case where the ultrasound transducer unit 46 receives the ultrasound wave.

The B mode image generation unit 162 is an image generation unit that generates a B mode image that is a tomographic image of the inside of the patient (inside of the body cavity). For the sequentially generated sound ray signals, the B mode image generation unit 162 corrects the attenuation due to the propagation distance according to the depth of the reflection position of the ultrasound wave by sensitivity time control (STC). The B mode image generation unit 162 performs envelope detection processing and logarithm (Log) compression processing on the corrected sound ray signal, thereby generating a B mode image (image signal).

The PW mode image generation unit 164 is an image generation unit that generates an image showing the speed of blood flow in a predetermined direction. The PW mode image generation unit 164 extracts a frequency component by applying a fast Fourier transform to a plurality of sound ray signals in the same direction among the sound ray signals sequentially generated by the phase matching unit 160. Thereafter, the PW mode image generation unit 164 calculates the speed of blood flow from the extracted frequency component, and generates a PW mode image (image signal) showing the calculated speed of blood flow.

The CF mode image generation unit 166 is an image generation unit that generates an image showing blood flow information in a predetermined direction. The CF mode image generation unit 166 generates an image signal indicating the blood flow information by calculating the autocorrelation between a plurality of sound ray signals in the same direction among the sound ray signals sequentially generated by the phase matching unit 160. Thereafter, based on the image signal described above, the CF mode image generation unit 166 generates a CF mode image (image signal) as a color image in which the blood flow information is superimposed on the B mode image signal generated by the B mode image generation unit 162.

The memory controller 151 stores the image signal generated by the B mode image generation unit 162, the PW mode image generation unit 164, or the CF mode image generation unit 166 in the cine memory 150.

The DSC 154 is connected to the ASIC 148, and converts (raster conversion) the signal of the image generated by the B mode image generation unit 162, the PW mode image generation unit 164, or the CF mode image generation unit 166 into an image signal according to a normal television signal scanning method, performs various kinds of required image processing, such as gradation processing, on the image signal, and then outputs an obtained signal to the monitor 20.

The cine memory 150 has a capacity for storing an image signal for one frame or several frames. The image signal generated by the ASIC 148 is output to the DSC 154, and is also stored in the cine memory 150 by the memory controller 151. In the freeze mode, the memory controller 151 reads the image signal stored in the cine memory 150 and outputs the read image signal to the DSC 154. As a result, an ultrasound image (still image) based on the image signal read from the cine memory 150 is displayed on the monitor 20.

The trigger generation circuit 156 generates a trigger for causing the CPU 152 to start polarization processing. The cause of generation of a trigger will be described later.

The CPU 152 functions as a controller (control circuit) that controls each unit of the ultrasound processor apparatus 14. The CPU 152 is connected to the reception circuit 142, the transmission circuit 144, the A/D converter 146, and the ASIC 148 to control these devices. Specifically, the CPU 152 is connected to the console 100, and controls each unit of the ultrasound processor apparatus 14 according to examination information, control parameters, and the like input through the console 100.

The CPU 152 automatically recognizes the ultrasound endoscope 12 based on a method, such as Plug and Play (PnP), in a case where the ultrasound endoscope 12 is connected to the ultrasound processor apparatus 14 through the ultrasound connector 32*a*. Thereafter, the CPU 152 accesses the endoscope side memory 58 of the ultrasound endoscope 12 to read the cumulative driving time stored in the endoscope side memory 58.

In addition, the CPU 152 accesses the endoscope side memory 58 at the end of the ultrasound diagnosis, and updates the cumulative driving time stored in the endoscope side memory 58 to a value obtained by adding the time required for the ultrasound diagnosis performed immediately before to the cumulative driving time stored in the endoscope side memory 58.

In the present embodiment, the cumulative driving time is stored on the ultrasound endoscope 12 side. However, the invention is not limited thereto, and the cumulative driving time may be stored on the ultrasound processor apparatus 14 side for each ultrasound endoscope 12.

The CPU 152 is connected to the trigger generation circuit 156. In a case where a trigger is given from the trigger generation circuit 156, the CPU 152 controls the transmission circuit 144 (pulse generation circuit 158) in a non-diagnosis period within each frame time during the execution period of the ultrasound diagnosis to generate a polarization driving pulse, which is a pulsed driving voltage, and supplies the polarization driving pulse to each of the plurality of ultrasound transducers 48 of the ultrasound transducer array 50 to perform polarization processing of each ultrasound transducer 48. More specifically, after a trigger is given from the trigger generation circuit 156, during the execution period of the ultrasound diagnosis, in a non-diagnosis period which is a period other than a period for acquiring an image of each frame and during which transmission of ultrasound waves and reception of reflected waves for performing ultrasound diagnosis are not performed, within each frame time in which an image (still image) of each frame of an ultrasound image (moving image) is acquired, a polarization driving pulse is supplied to each of the plurality of ultrasound transducers 48 to perform polarization processing.

In the invention, the polarization driving pulse is generated by the transmission circuit 144 that generates a diagnostic driving pulse for acquiring an ultrasound image. That is, the transmission circuit 144 has the same circuit configuration as an existing transmission circuit that does not have a new circuit configuration for generating the polarization driving pulse. Here, the transmission circuit 144 has a settable voltage range in which at least two driving voltages of an image driving voltage for a diagnostic driving pulse and a polarization driving voltage for a polarization driving pulse can be set. The driving voltage is set to the image driving voltage within the settable voltage range in the case of acquiring an ultrasound image, and the driving voltage is set to the polarization driving voltage, which is different from the image driving voltage, within the same settable voltage range in the case of performing polarization processing. In the invention, the polarization driving voltage is preferably set to a voltage higher than the image driving voltage, more preferably to a higher voltage within the settable voltage range, and most preferably to the upper limit voltage.

Although the details will be described later, the polarization driving pulse (main lobe) is a driving pulse in a frequency band different from the probe frequency band of the diagnostic driving pulse.

Therefore, the driving voltage applied to the ultrasound transducer 48 at the time of polarization processing is different from the driving voltage applied to the ultrasound transducer 48 at the time of acquisition of an ultrasound image, and can be said to be a higher voltage than the driving voltage applied to the ultrasound transducer 48 at the time of acquisition of an ultrasound image. In addition, the polarization driving pulse wave applied to the ultrasound transducer 48 at the time of polarization processing is generated by the same transmission circuit 144 as for the diagnostic driving pulse wave applied to the ultrasound transducer 48 at the time of acquisition of an ultrasound image, and can be said to be a polarization driving voltage different from voltage of the image driving pulse within the same settable voltage range as the image driving pulse wave and be a driving pulse having a frequency different from the probe frequency band for acquiring an ultrasound image.

From the above, the invention has an existing transmission circuit configuration. Using the transmission circuit 144 for the same driving pulse output as acquisition of an ultrasound image, a driving voltage within the same settable voltage range as the diagnostic driving pulse for acquiring an ultrasound image and a polarization driving pulse having a frequency different from the probe frequency band are output, and polarization processing of the ultrasound transducer 48 of the ultrasound endoscope 12 is performed at a time different from the time for acquiring an ultrasound image.

The magnitude (voltage value or potential) of the driving voltage of the polarization driving pulse is set to an appropriate value satisfying the conditions for obtaining the repolarization effect, within the settable voltage range of the transmission circuit 144, by the CPU 152 in accordance with the specification of the ultrasound transducer 48 (specifically, the thickness and the material of the ultrasound transducer 48) provided in the ultrasound endoscope 12 connected to the ultrasound processor apparatus 14. The supply time of the driving voltage of the polarization driving pulse is set to an appropriate value satisfying the conditions for obtaining the repolarization effect by the CPU 152 in accordance with the specification of the ultrasound transducer 48 (specifically, the thickness and the material of the ultrasound transducer 48). Thereafter, the CPU 152 performs polarization processing based on the set values described above.

That is, in the invention, in the case of acquiring an ultrasound image, the CPU (control circuit) 152 controls the transmission circuit 144 (pulse generation circuit 158) to generate a diagnostic driving pulse (transmission signal) to be applied to each of the plurality of ultrasound transducers 48 that generate ultrasound waves for acquisition of an ultrasound image.

On the other hand, in the case of performing polarization processing, in order to perform polarization processing of the plurality of ultrasound transducers 48, the CPU (control circuit) 152 controls a transmission circuit to generate a polarization driving pulse that has a frequency different from the probe frequency band as an ultrasound probe (ultrasound transducer unit 46) for acquiring an ultrasound image and that has a polarization driving voltage different from voltage of the diagnostic driving pulse within the same settable voltage range as the diagnostic driving pulse.

As a result, in the invention, in the case of performing polarization processing, the polarization driving pulse is applied to the plurality of ultrasound transducers 48, and the polarization processing of the plurality of ultrasound transducers 48 is performed by the polarization driving pulse.

Next, a pulse waveform and a driving waveform (transmission waveform) of a polarization driving pulse (transmission wave for polarization) transmitted from the transmission circuit 144 to the ultrasound transducer 48 in the invention will be described.

Figure 5A:
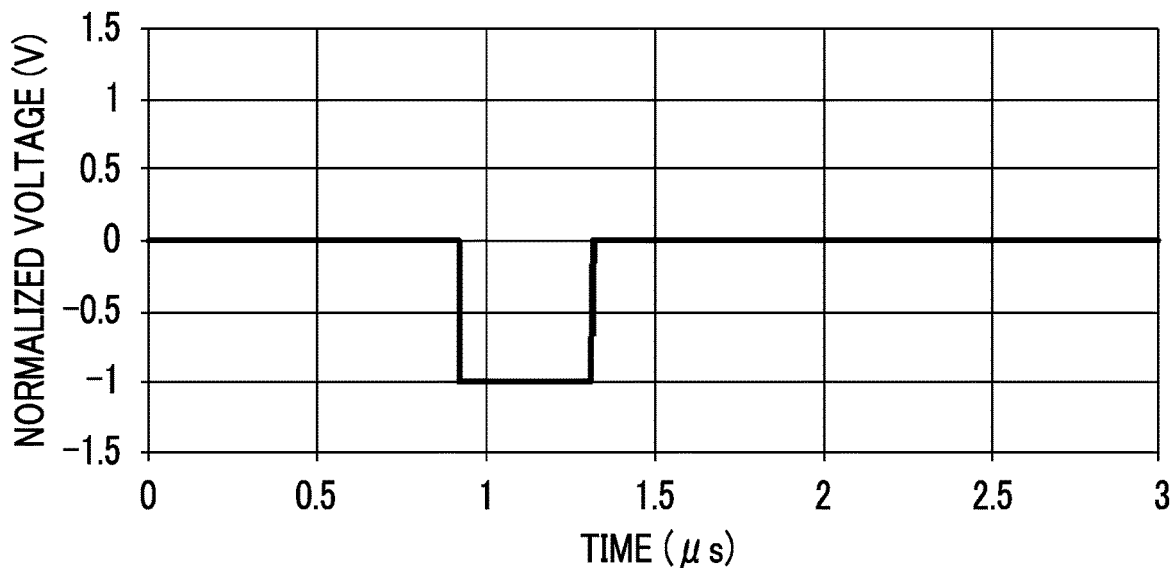
FIG. 5A is a graph showing an example of a driving waveform of a polarization driving pulse transmitted from a transmission circuit shown in FIG. 4.
Figure 5B:
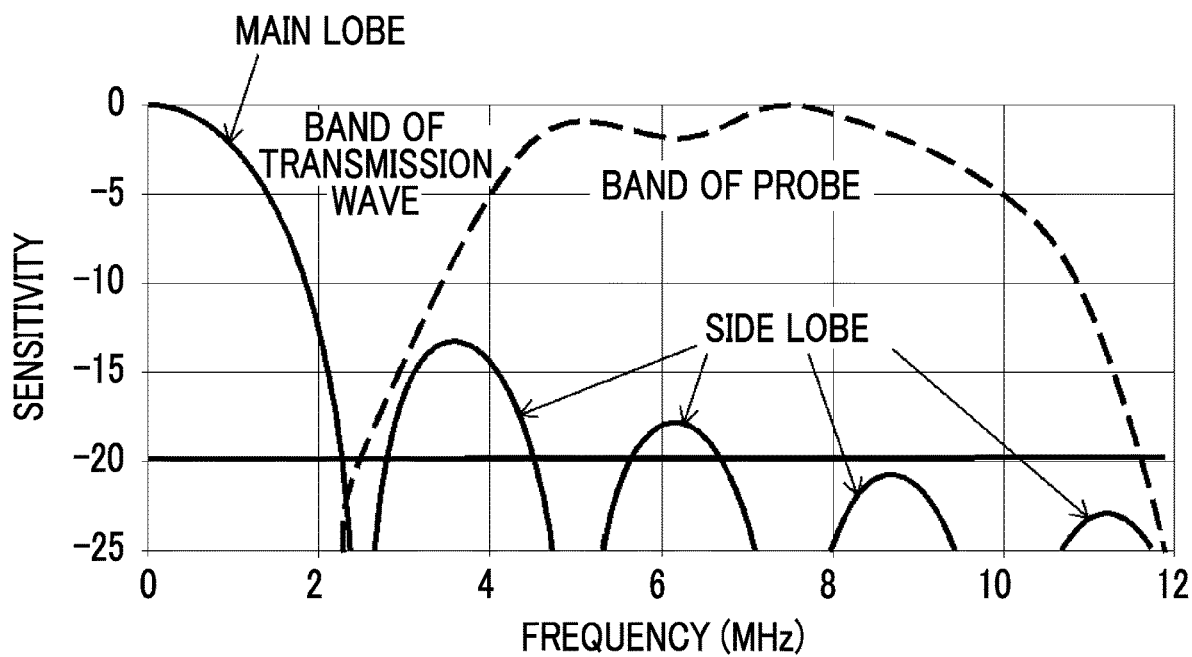
FIG. 5B is a graph showing the relationship between the frequency and the sensitivity of the driving waveform of the polarization driving pulse shown in FIG. 5A.

FIGS. 5A and 5B are graphs of an example of a driving waveform of a polarization driving pulse transmitted from the transmission circuit shown in FIG. 4, and are graphs showing the relationship between the sensitivity and the frequency of the driving waveform. The driving waveform shown in FIG. 5A is a waveform of one unipolar wave having a frequency of 1.25 MHz.

In the invention, the driving waveform of the polarization driving pulse is not particularly limited, but preferably has a unipolar waveform shown in FIG. 5A, and it is preferable to perform polarization processing of the ultrasound transducer 48 using a polarization driving pulse having a driving waveform having a frequency characteristic shown by the solid line in FIG. 5B. In the example shown in FIG. 5B, for example, at a sensitivity level of −20 dB or more, the probe frequency band for acquiring an ultrasound image is about 2.7 MHz to about 11.7 MHz as shown by the broken line, while the band of the main lobe of the driving waveform of the polarization driving pulse shown by the solid line is about 2.3 MHz or less. That is, the band characteristic of the frequency of the polarization driving pulse and the band characteristic of the frequency of the diagnostic driving pulse do not overlap each other at a sensitivity level of −20 dB or more.

That is, in the invention, as shown in FIG. 5B, in the driving waveform of the polarization driving pulse, it is preferable that the frequency band of the main lobe and the probe frequency band shown by the broken line do not overlap each other at a sensitivity level of −20 dB or more. In addition, it is preferable that the frequency band of the main lobe is lower than the probe frequency band at a sensitivity level of −20 dB or more. The reason is that, in the polarization processing, it is necessary to reduce an influence on the ultrasound image by preventing excessive ultrasound wave output and to reduce an influence on the body cavity of the subject due to temperature rise by preventing the temperature rise. In particular, the upper limit temperature of the distal end portion of the ultrasound endoscope 12 inserted into the body cavity of the subject is strictly limited so as not to affect the body cavity and the like, and it is necessary to prevent the temperature rise.

In the invention, since the polarization driving pulse (main lobe) is transmitted outside the probe frequency band, the energy input to the ultrasound transducer 48 is reduced. Therefore, the temperature rise can be suppressed. In addition, since the outside of the probe frequency band is the outside of a resonance band in which the ultrasound transducer 48 resonates. Accordingly, the output sound pressure is reduced even though the polarization driving pulse (main lobe) is applied to the ultrasound transducer 48.

In the driving waveform of the polarization driving pulse shown in FIG. 5B, it can be seen that, in addition to the main lobe, within the probe frequency band, one or more side lobes similarly shown by the solid line (in the example shown in FIG. 5B, four side lobes) are generated. As shown in FIG. 5B, it is preferable that all the maximum sensitivities of the side lobes within the probe frequency band are equal to or less than −10 dB and the average sensitivity of the side lobes is equal to or less than −20 dB. The reason is as follows.

In general, the specification of the frequency characteristic of the probe is expressed in the −20 dB band of the transmission and reception sensitivity. This is because the signal of 1/10 or less from the peak of the sensitivity hardly affects an image. On the other hand, the band of the transmission wave is different from that in the case of the probe. Since only a transmission portion is taken into consideration, the level of 20 dB/2=10 dB is the threshold value. For this reason, −10 dB is more preferable in a case where a transmission component is considered.

Figure 6A:
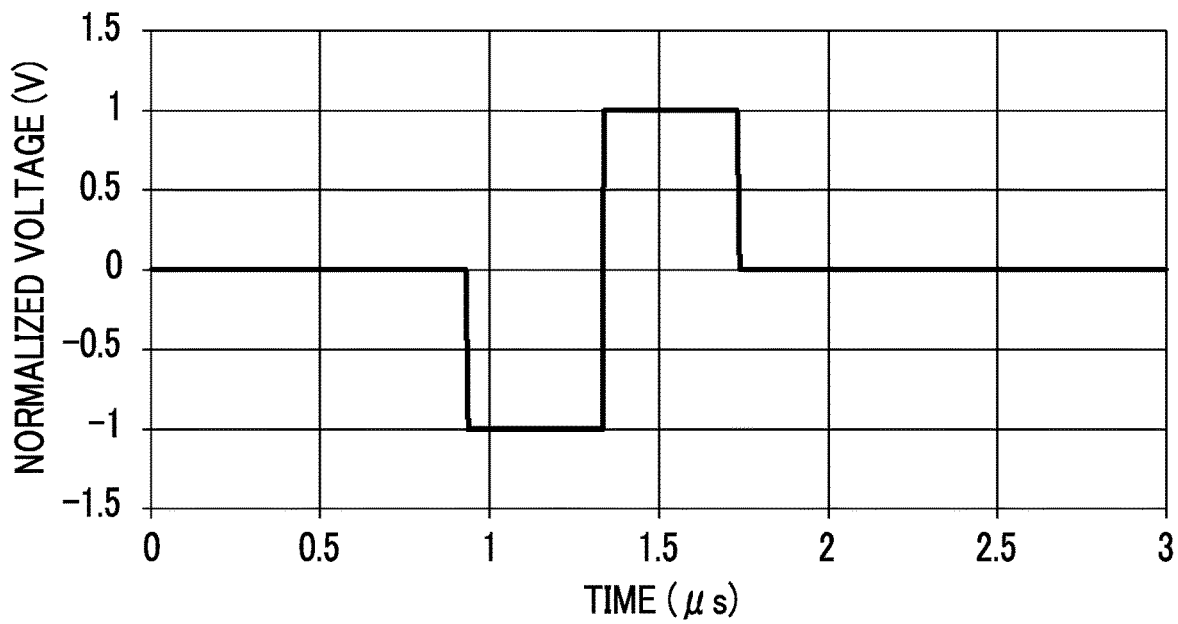
FIG. 6A is a graph showing another example of the driving waveform of the polarization driving pulse transmitted from the transmission circuit shown in FIG. 4.
Figure 6B:
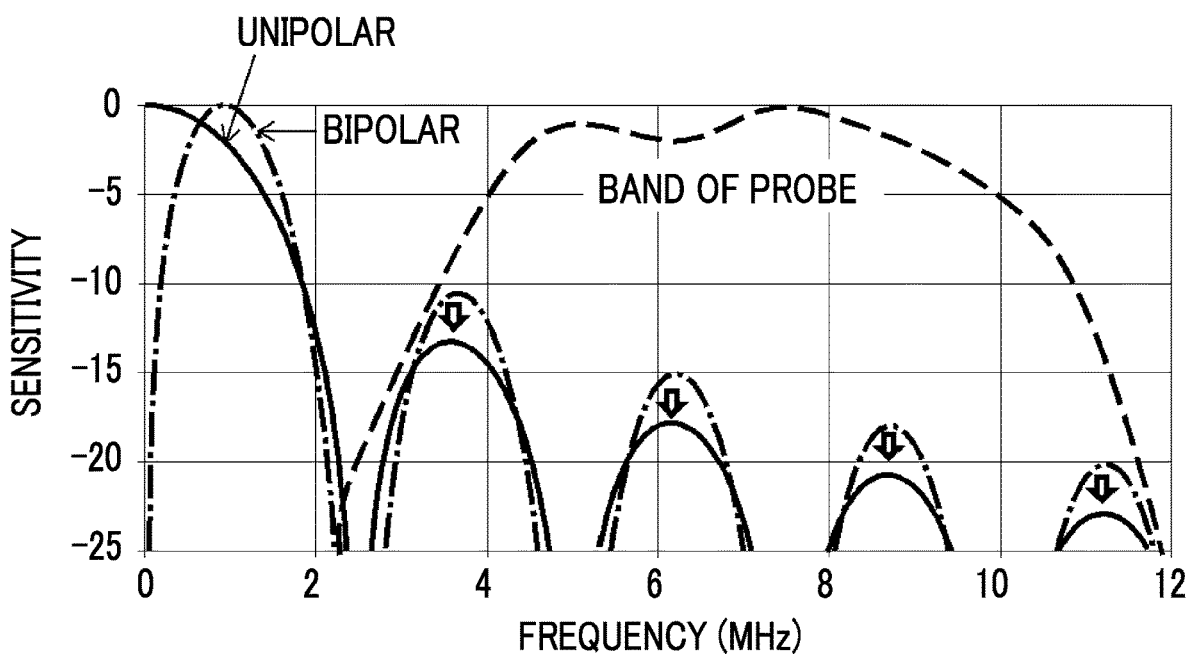
FIG. 6B is a graph showing the relationship between the frequency and the sensitivity of the driving waveform of the polarization driving pulse shown in FIG. 5A and the relationship between the frequency and the sensitivity of the driving waveform of the polarization driving pulse shown in FIG. 6A.

In the invention, the driving waveform of the polarization driving pulse is not particularly limited, and may be a bipolar waveform shown in FIG. 6A. However, the driving waveform of the polarization driving pulse is preferably a unipolar waveform as shown in FIG. 5A. The reason is that, as in the frequency characteristic of the driving waveform shown in FIG. 6B, the sensitivity of the main lobe does not change whether the driving waveform is a unipolar waveform shown by the solid line or a bipolar waveform shown by the one-dot chain line, but the sensitivities of all of the four side lobes in the case of the unipolar waveform are lower than those in the case of the bipolar waveform.

Therefore, by forming the transmission waveform as a unipolar waveform as shown in FIG. 5A, not only the main lobe but harmonic components can be suppressed. As a result, higher effects can be expected.

Figure 7A:
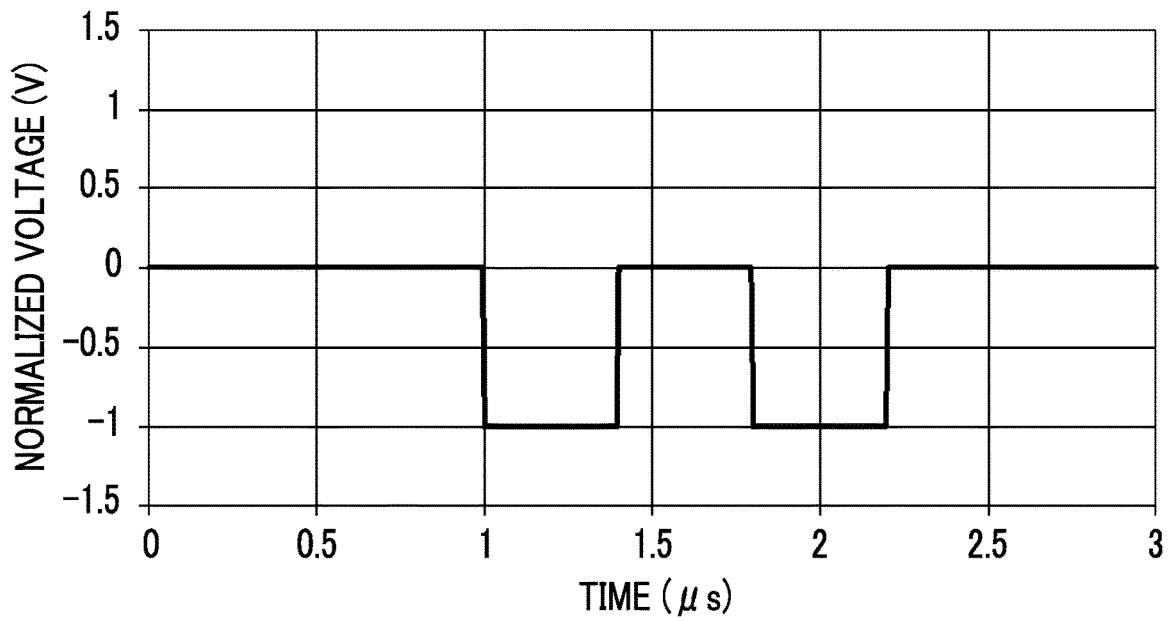
FIG. 7A is a graph showing another example of the pulse waveform of the polarization driving pulse transmitted from the transmission circuit shown in FIG. 4.
Figure 7B:
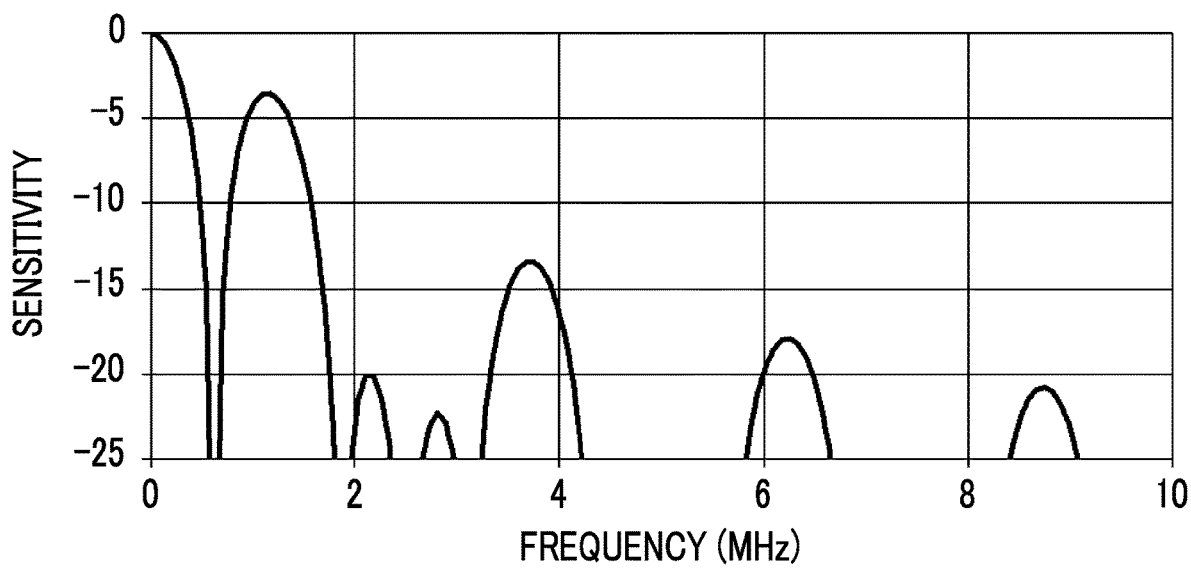
FIG. 7B is a graph showing the relationship between the frequency and the sensitivity of the driving waveform of the polarization driving pulse shown in FIG. 7A.

As shown in FIG. 7A, a plurality of unipolar waveforms may be transmitted as the polarization driving pulses. In the example shown in FIG. 7A, two pulse waves may be transmitted. The polarization driving pulse shown in FIG. 7A has a driving waveform including two pulse waves as a driving waveform of the polarization driving pulse shown in FIG. 5A. The frequency characteristic of the driving waveform of the polarization driving pulse shown in FIG. 7A is shown in FIG. 7B. The frequency characteristic of the driving waveform shown in FIG. 7B is different from the frequency characteristic of the driving waveform shown in FIG. 5B in terms of the waveform of the main lobe, but the waveform of the side lobe does not change much.

Figure 7C:
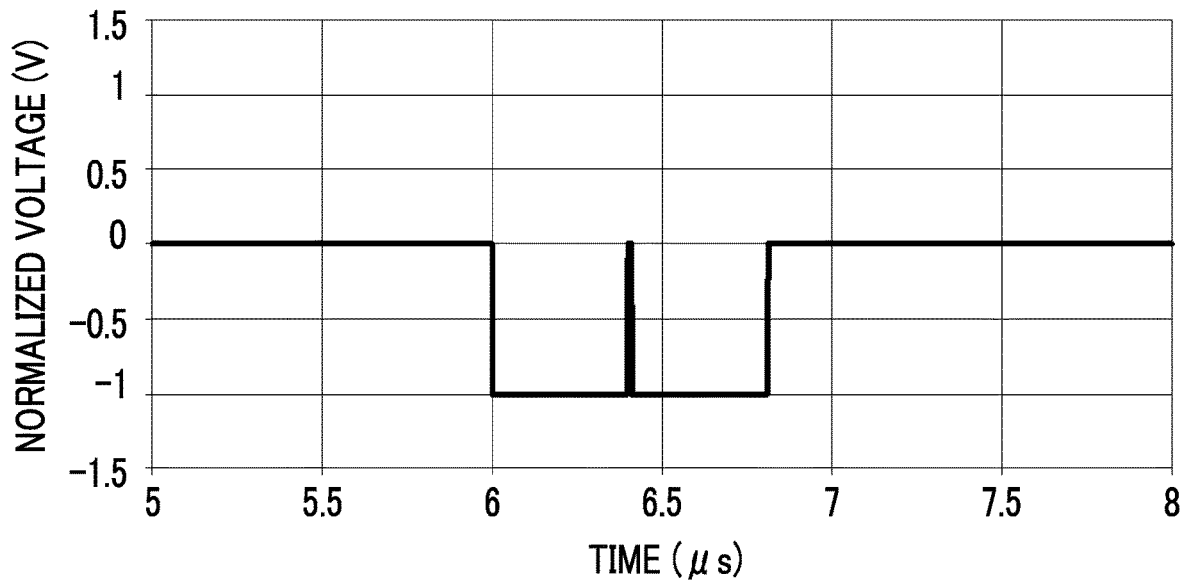
FIG. 7C is a graph showing another example of the pulse waveform of the polarization driving pulse transmitted from the transmission circuit shown in FIG. 4.

In addition, as shown in FIG. 7C, it is preferable to transmit a polarization driving pulse in which a plurality of pulse waveforms are connected to each other with the time of the minimum number of clocks between driving waveforms of the polarization driving pulse as unipolar waveforms. That is, in the invention, it is preferable that the transmission circuit 144 outputs a plurality of unipolar waveforms as polarization driving pulses with the time of the minimum number of clocks defined in the ultrasound processor apparatus 14 as an interval between the unipolar waveforms.

The reason is that it is optimal to apply a DC voltage for polarization processing, but the DC voltage cannot be transmitted in a case where the transmission circuit 144 having an existing transmission circuit configuration is used as in the invention.

The minimum and maximum time widths are determined depending on the type of pulser (pulse generation circuit 158) of the transmission circuit 144 of the ultrasound processor apparatus 14 used in the ultrasound diagnostic apparatus 10. Therefore, by using the time of the minimum number of clocks defined in the transmission circuit 144 as the minimum time width, a high repolarization effect can be expected by putting the minimum time width between a plurality of unipolar waveforms so that a polarization processing waveform close to a DC voltage is obtained. The minimum time width between two unipolar pulse waveforms, that is, the minimum pulse width is determined by the specification of the pulser (pulse generation circuit 158) of the transmission circuit 144. Control to comply with this specification is provided from the above-described FPGA in the transmission circuit 144.

Figure 7D:
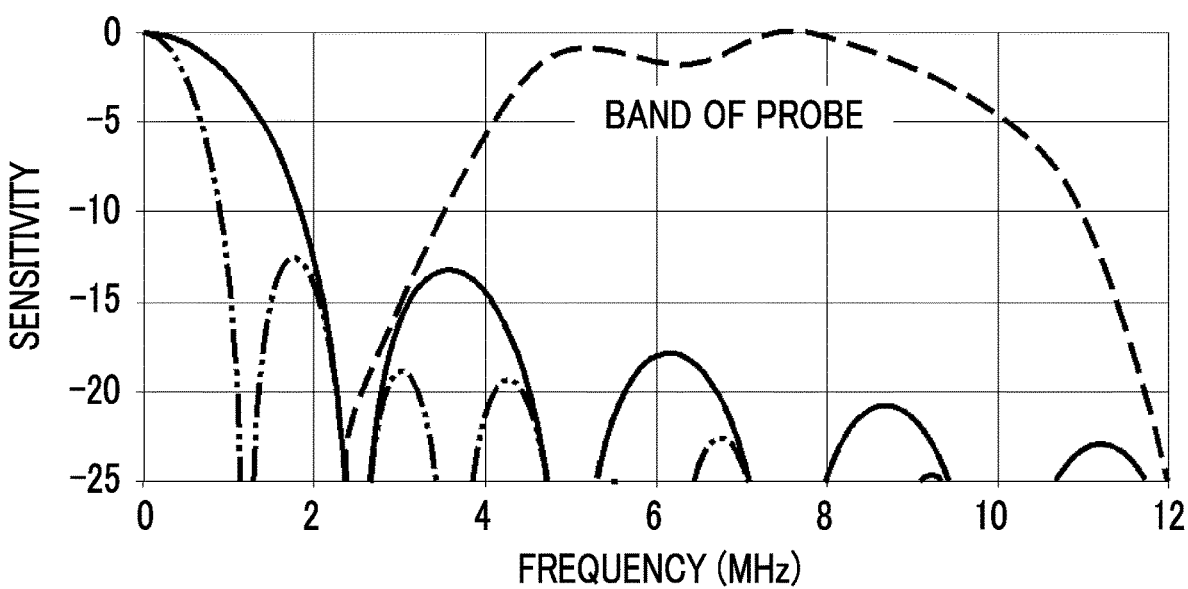
FIG. 7D is a graph showing the relationship between the frequency and the sensitivity of the driving waveform of the polarization driving pulse shown in FIG. 7C.

As shown by a two-dot chain line in FIG. 7D, by using a combination of a plurality of unipolar waveforms shown in FIG. 7C as the driving waveform of the polarization driving pulse, it is possible to reduce the maximum sensitivity of the side lobe more than in the case of the driving waveform of the polarization driving pulse including one unipolar waveform shown by the solid line in FIG. 7D.

Figure 8A:
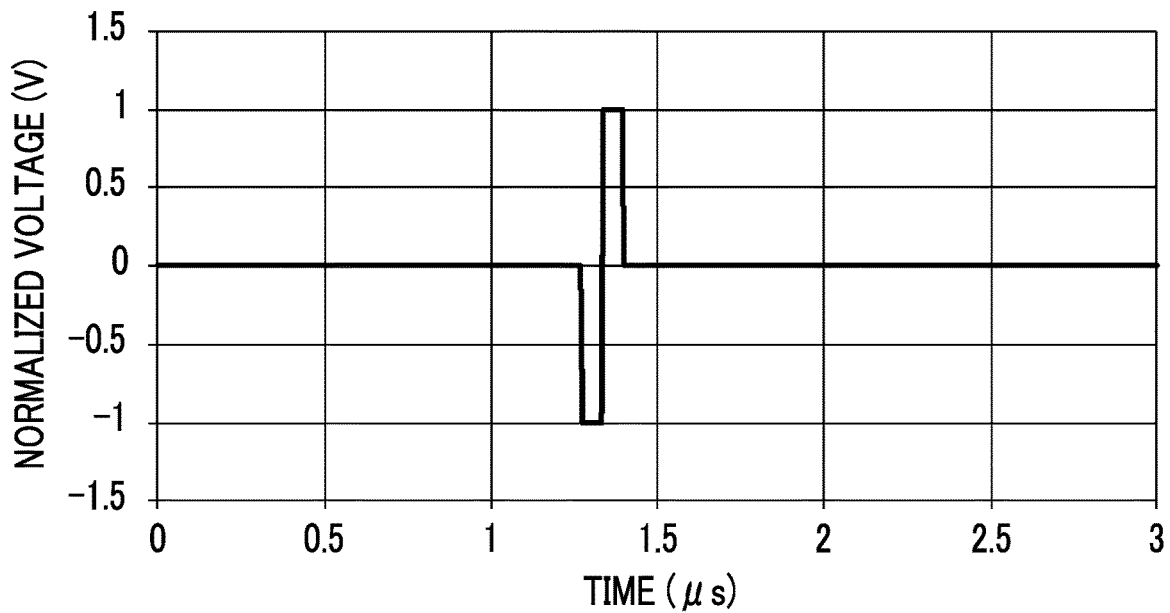
FIG. 8A is a graph showing another example of the pulse waveform of the diagnostic driving pulse transmitted from the transmission circuit shown in FIG. 4.
Figure 8B:
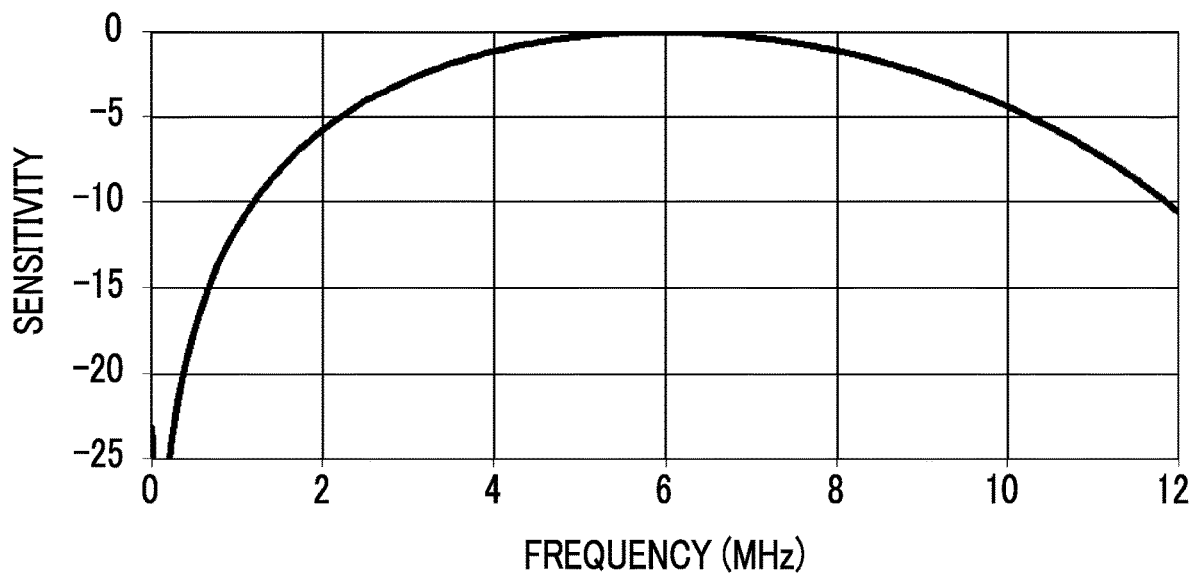
FIG. 8B is a graph showing the relationship between the frequency and the sensitivity of the driving waveform of the diagnostic driving pulse shown in FIG. 8A.

On the other hand, FIGS. 8A and 8B are graphs of an example of a driving waveform of a diagnostic driving pulse transmitted from the transmission circuit shown in FIG. 4, and are graphs showing the relationship between the sensitivity and the frequency of the driving waveform. The driving waveform shown in FIG. 8A is a waveform of one bipolar wave having a center frequency of 6 MHz. The frequency characteristic of the driving waveform of the diagnostic driving pulse is shown in FIG. 8B.

<<Operation Example of Ultrasound Diagnostic Apparatus>>

Figure 9:
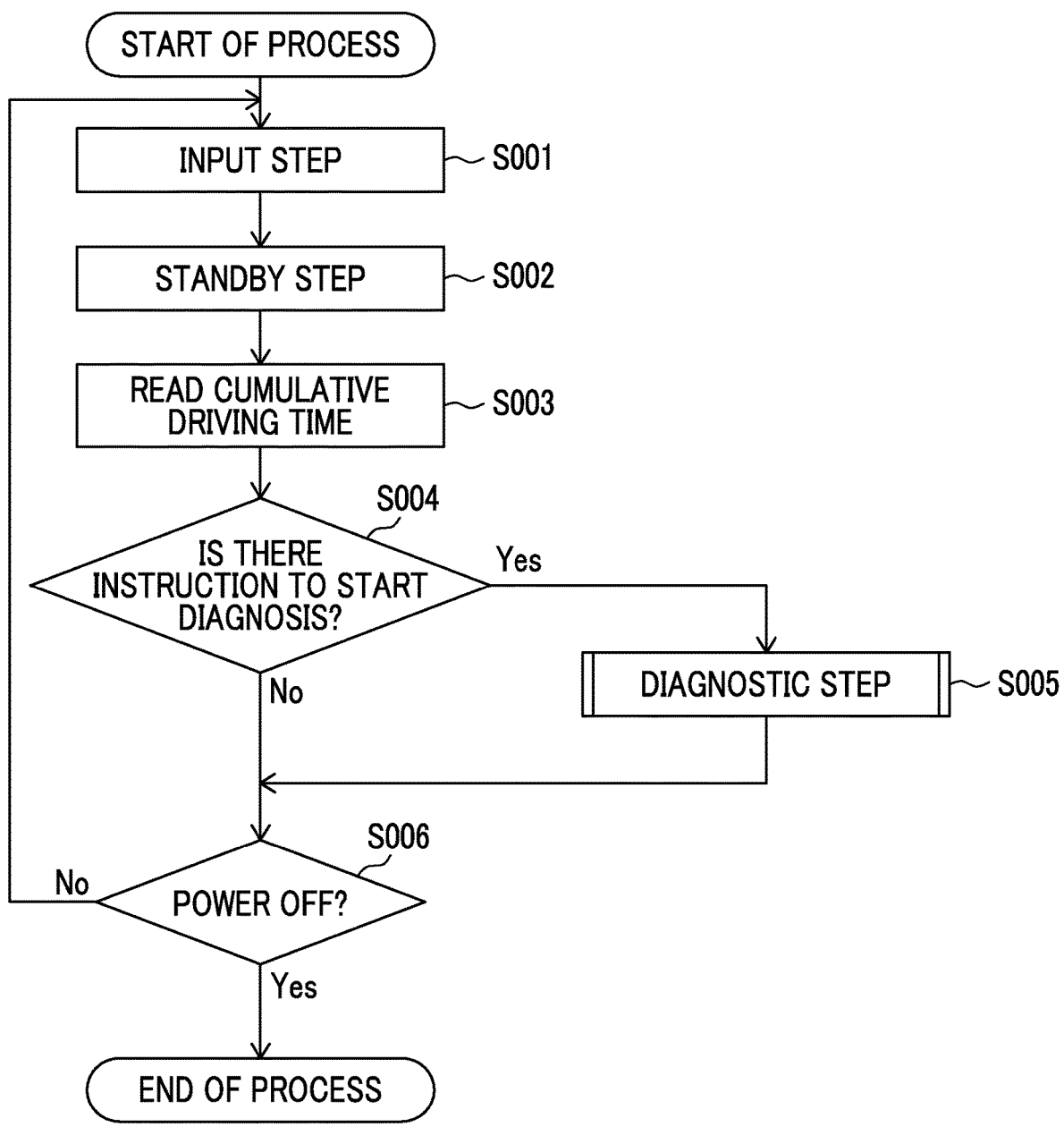
FIG. 9 is a diagram showing the flow of the diagnostic process using the ultrasound diagnostic apparatus shown in FIG. 1.
Figure 10:
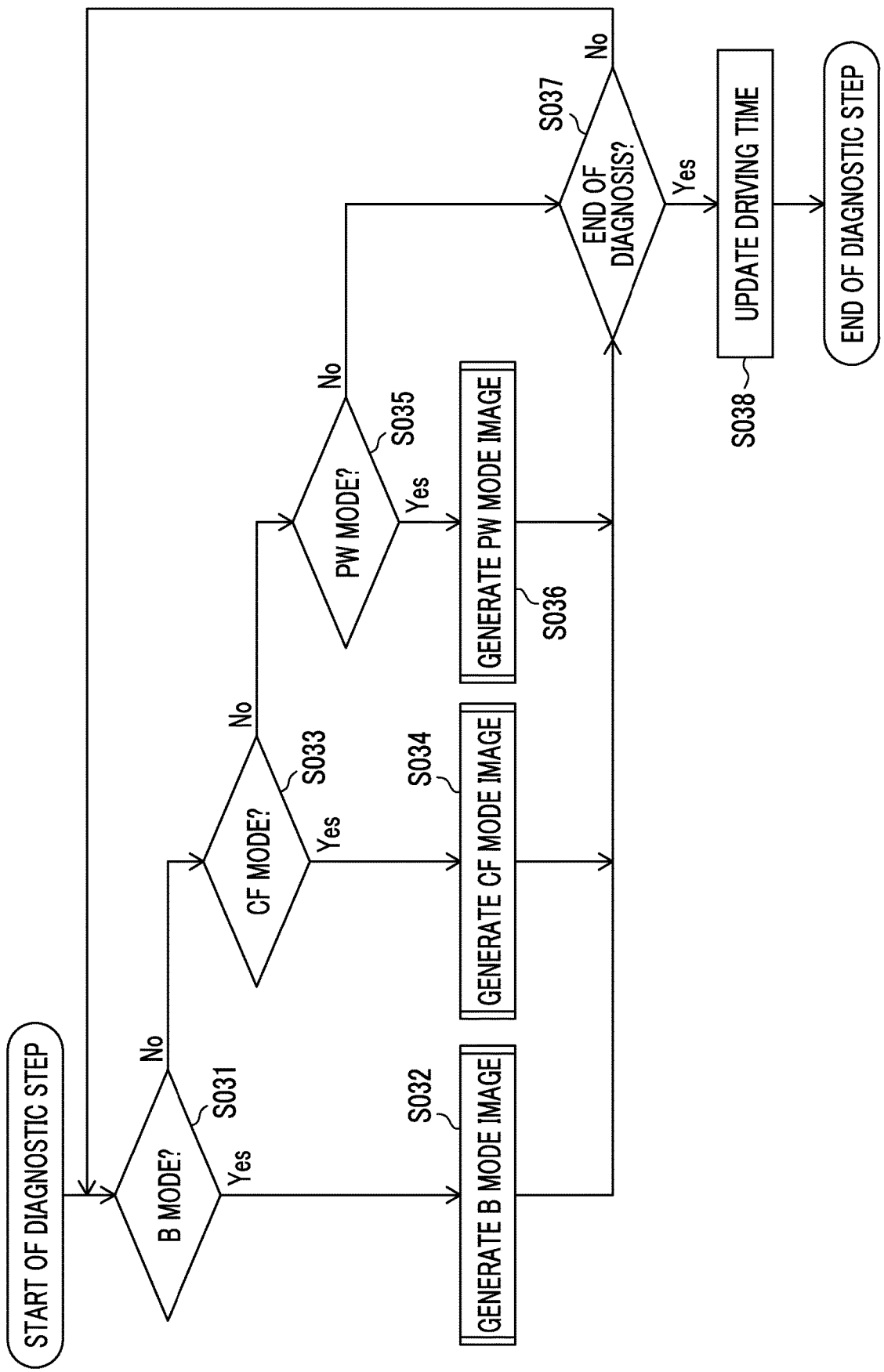
FIG. 10 is a diagram showing the procedure of a diagnostic step in the diagnostic process.
Figure 11:
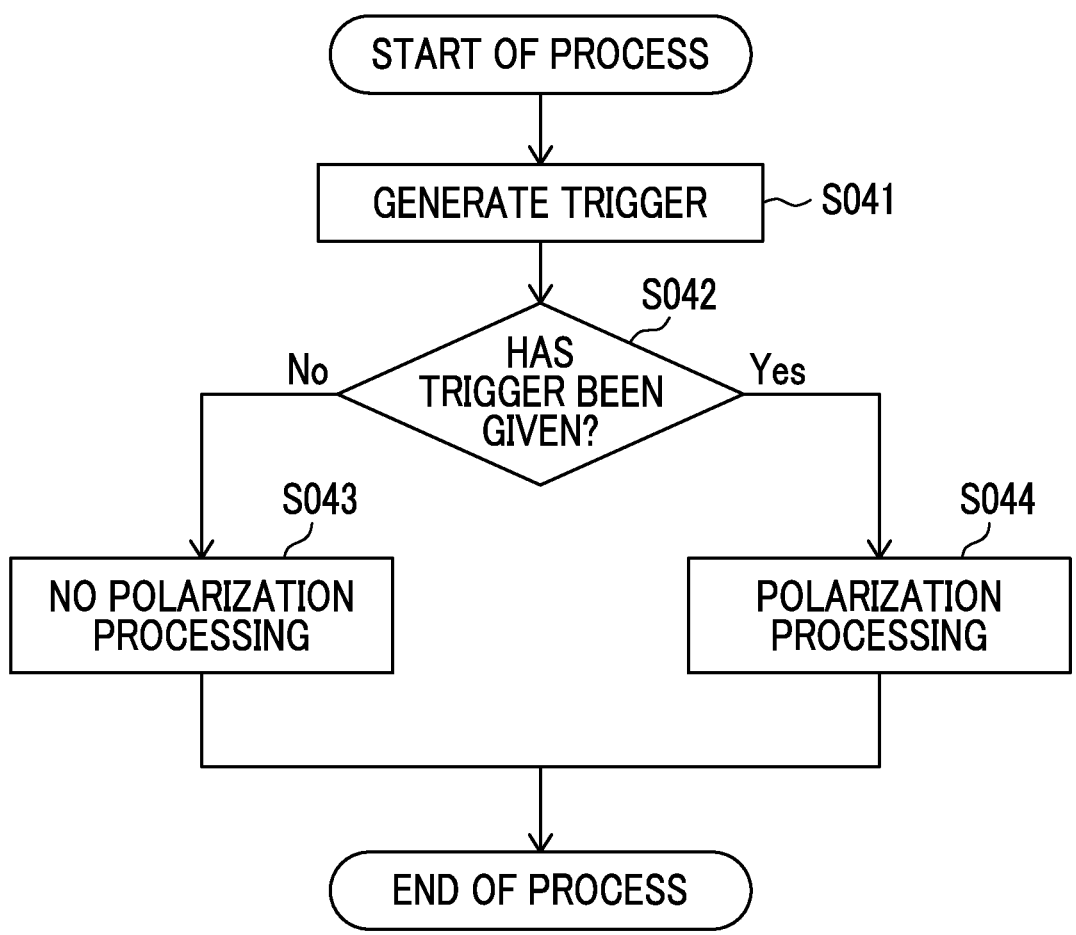
FIG. 11 is a diagram showing the flow of a process in the case of performing polarization processing.

Next, as an operation example of the ultrasound diagnostic apparatus 10, a flow of a series of processes relevant to ultrasound diagnosis (hereinafter, also referred to as diagnostic process) will be described with reference to FIGS. 9 to 11. FIG. 9 is a diagram showing the flow of the diagnostic process using the ultrasound diagnostic apparatus 10. FIG. 10 is a diagram showing the procedure of a diagnostic step in the diagnostic process. FIG. 11 is a diagram showing the flow of the process in the case of performing polarization processing in the diagnostic step.

In a case where each unit of the ultrasound diagnostic apparatus 10 is powered on in a state in which the ultrasound endoscope 12 is connected to the ultrasound processor apparatus 14, the endoscope processor apparatus 16, and the light source device 18, the diagnostic process starts with the power-ON as a trigger. In the diagnostic process, as shown in FIG. 9, an input step is performed first (S001). In the input step, the operator inputs examination information, control parameters, and the like through the console 100. In a case where the input step is completed, a standby step is performed until there is an instruction to start diagnosis (S002). Using the standby step, the CPU 152 of the ultrasound processor apparatus 14 reads a cumulative driving time from the endoscope side memory 58 of the ultrasound endoscope 12 (S003).

Then, in a case where there is an instruction to start diagnosis from the operator (Yes in S004), the CPU 152 controls each unit of the ultrasound processor apparatus 14 to perform a diagnostic step (S005). The diagnostic step proceeds along the flow shown in FIG. 10. In a case where the designated image generation mode is the B mode (Yes in S031), each unit of the ultrasound processor apparatus 14 is controlled so as to generate a B mode image (S032). In a case where the designated image generation mode is not the B mode (No in S031) but the CF mode (Yes in S033), each unit of the ultrasound processor apparatus 14 is controlled so as to generate a CF mode image (S034). In a case where the designated image generation mode is not the CF mode (No in S033) but the PW mode (Yes in S035), each unit of the ultrasound processor apparatus 14 is controlled so as to generate a PW mode image (S036). In a case where the designated image generation mode is not the PW mode (No in S036), the process proceeds to step S037.

In each image generation mode, as shown in FIG. 11, the trigger generation circuit 156 generates a trigger for starting polarization processing, and the trigger is given from the trigger generation circuit 156 to the CPU 152 (S041).

The CPU 152 determines whether or not the trigger has been given from the trigger generation circuit 156 (S042).

In a case where no trigger is given to the CPU 152 (No in S042), the CPU 152 controls each unit of the ultrasound processor apparatus 14 so that the normal ultrasound diagnosis is performed. That is, the polarization processing is not performed during the execution period of the ultrasound diagnosis (S043).

On the other hand, in a case where a trigger is given to the CPU 152 (Yes in S042), the CPU 152 controls each unit of the ultrasound processor apparatus 14 so that polarization processing is performed on the plurality of ultrasound transducers 48 in a non-diagnosis period, which is a period other than a period for acquiring an image of each frame and during which transmission of ultrasound waves and reception of reflected waves for performing ultrasound diagnosis are not performed, within each frame time in which an image of each frame of an ultrasound image is acquired during the execution period of the ultrasound diagnosis after the trigger is given. That is, the polarization processing is performed during the execution period of the ultrasound diagnosis (S044).

Then, returning to FIG. 10, the CPU 152 determines whether or not the ultrasound diagnosis has ended (S037). In a case where the ultrasound diagnosis has not ended (No in S037), the process returns to the diagnostic step S031, and the generation of an ultrasound image in each image generation mode is repeatedly performed until the diagnosis end conditions are satisfied. As the diagnosis end conditions, for example, the operator gives an instruction to end the diagnosis through the console 100.

On the other hand, in a case where the diagnosis end conditions are satisfied and accordingly the ultrasound diagnosis ends (Yes in S037), the CPU 152 adds the time required for the ultrasound diagnosis performed so far to the cumulative driving time read out from the endoscope side memory 58 in step S003, and updates the cumulative driving time stored in the endoscope side memory 58 to the cumulative driving time after the addition (S038). The diagnostic step ends at a point in time at which the series of steps (steps S031 to S038) in the diagnostic step end.

Then, returning to FIG. 9, the diagnostic process ends at a point in time at which each unit of the ultrasound diagnostic apparatus 10 is powered off (Yes in S006). On the other hand, in a case where the power of each unit of the ultrasound diagnostic apparatus 10 is maintained in the ON state (No in S006), the process returns to the input step S001, and each step of the diagnostic process described above is repeated.

Next, the scanning timing of a scanning line (line) scanned by electronic sector scanning in the case of performing ultrasound diagnosis will be described.

Figure 12:
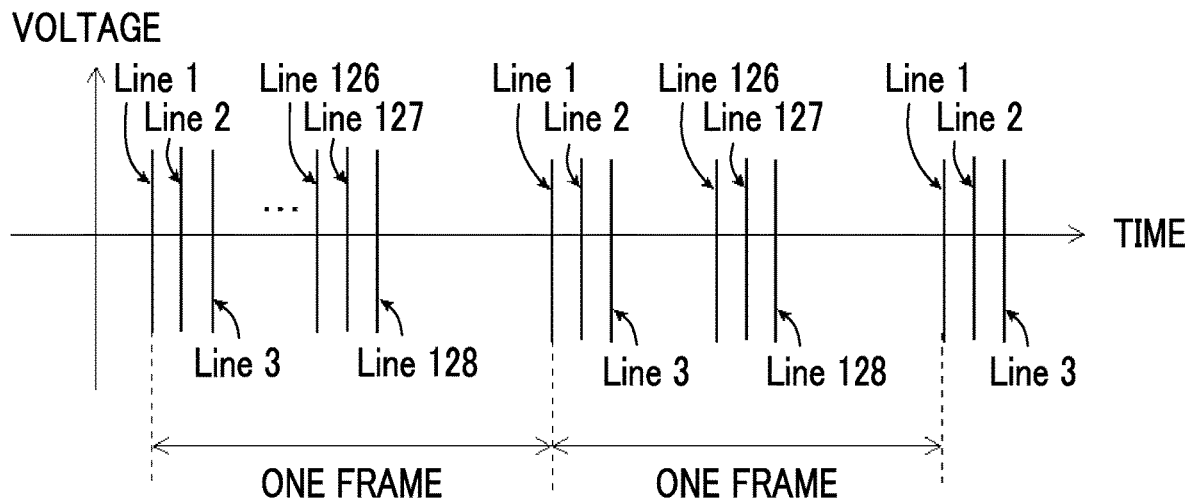
FIG. 12 is a conceptual diagram of an example showing the scanning timings of a plurality of scanning lines scanned by electronic sector scanning during the execution period of ultrasound diagnosis.

FIG. 12 is a conceptual diagram of an example showing the scanning timings of a plurality of scanning lines scanned by electronic sector scanning during the execution period of ultrasound diagnosis. In FIG. 12, the vertical axis indicates a voltage of a pulse (transmission pulse) of a transmission signal for generating an ultrasound wave for scanning a scanning line, and the horizontal axis indicates the passage of time.

Figure 13:
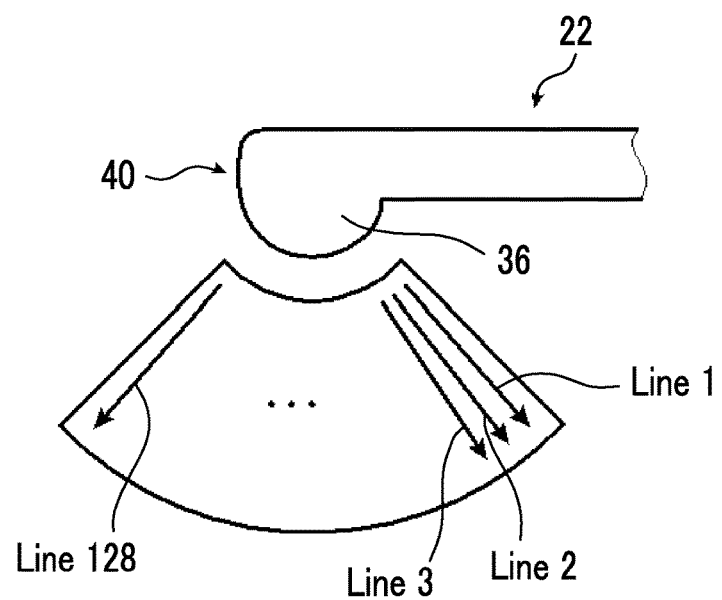
FIG. 13 is a conceptual diagram of an example showing a plurality of scanning lines.

In the present embodiment, it is assumed that the total number of plural ultrasound transducers 48 (the number of elements) is N=128 and the total number of scanning lines (lines) within each frame time, in which an image (still image) of each frame of an ultrasound image (moving image) is acquired, is 128 lines from a scanning line Line1 on the right end side to a scanning line Line128 on the left end side as shown in FIG. 13. In addition, it is assumed that the number of ultrasound transducers 48 (the number of opening channels) simultaneously driven to form an ultrasound beam at the time of ultrasound diagnosis is m=64.

A plurality of scanning lines Line1 to Line128 are scanned by electronic sector scanning for acquiring an image of one frame of an ultrasound image, and an ultrasound beam for scanning an image of each line of the ultrasound image is expressed as a virtual line.

In the case of performing ultrasound diagnosis, as shown in FIG. 12, during the execution period of the ultrasound diagnosis, that is, during a period from the start of acquisition of an ultrasound image (moving image) to the end of the acquisition, scanning of the scanning lines Line1 to Line128 is sequentially performed within each frame time in which an image of each frame of an ultrasound image is acquired. That is, a transmission signal (first transmission signal) having a driving voltage for performing ultrasound diagnosis is supplied from the transmission circuit 144 to the driving target transducer for performing ultrasound diagnosis.

Within each frame time, a period during which an ultrasound image is acquired is a period during which scanning of the scanning lines Line1 to Line128 is performed. In addition, a non-diagnosis period is a period from the end of scanning of the scanning line Line128 to the end of each frame time.

In the example shown in FIG. 12, between the end of scanning of the last scanning line Line128 within one frame time and the start of scanning of the first scanning line Line1 within the next one frame time, a non-diagnosis period is provided in which transmission of ultrasound waves and reception of reflected waves (echoes) of ultrasound waves for performing ultrasound diagnosis are not performed. In the case of the present embodiment, the non-diagnosis period is provided. However, the non-diagnosis period may not be provided depending on the system.

Next, the timing of supplying a transmission signal for performing polarization processing in the case of performing the polarization processing during the execution period of ultrasound diagnosis will be described.

Figure 14:
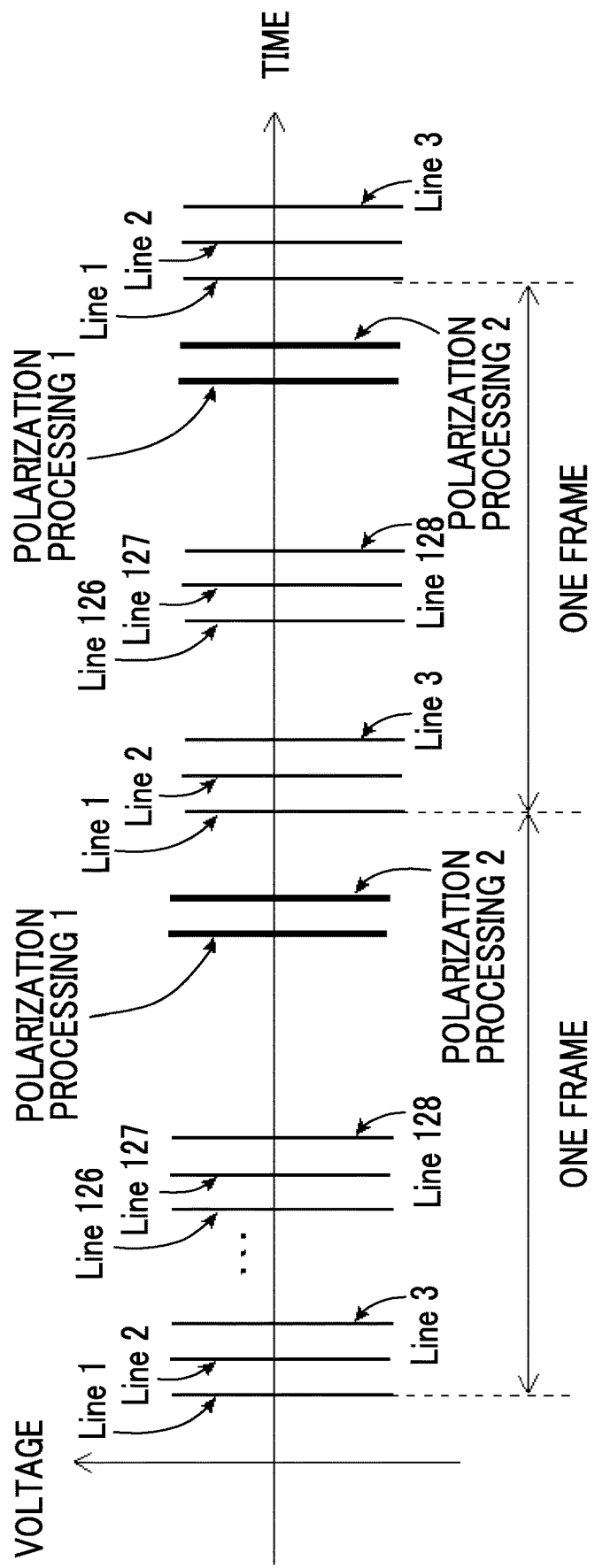
FIG. 14 is a conceptual diagram of an example showing the timing of scanning a scanning line and the timing of supplying a transmission signal for performing polarization processing in the case of performing polarization processing during the execution period of ultrasound diagnosis.

FIG. 14 is a conceptual diagram of an example showing the timing of scanning a scanning line and the timing of supplying a transmission signal for performing polarization processing in the case of performing polarization processing during the execution period of ultrasound diagnosis.

In the case of performing polarization processing, as shown in FIG. 14, within each frame time, scanning of the scanning lines Line1 to Line128 for performing ultrasound diagnosis is sequentially performed as in the case shown in FIG. 12. Then, within each frame time, polarization processing is performed in a non-diagnosis period after the end of the scanning of the last scanning line Line128. That is, a transmission signal (second transmission signal) having a polarization voltage for performing polarization processing is supplied from the transmission circuit 144 to the polarization target transducer that performs polarization processing.

In the case of the present embodiment, two transmission signals for polarization processing called polarization processing 1 and 2 are supplied as transmission signals for performing polarization processing. As described above, the total number of plural ultrasound transducers 48 is 128, and the number of opening channels is 64 that is the half of 128. Therefore, a transmission signal of polarization processing 1 is supplied to the 64 ultrasound transducers 48, which are the half of the 128 ultrasound transducers 48, and then a transmission signal of polarization processing 2 is supplied to the 64 ultrasound transducers 48, which are the remaining half.

The two transmission signals for polarization processing called polarization processing 1 and 2 are polarization driving pulses having driving waveforms shown in FIGS. 5 to 8 as described above. Therefore, the description of the polarization driving pulses of the transmission signals will be omitted herein.

In the case of the present embodiment, since a non-diagnosis period is provided within each frame time, it is possible to perform polarization processing without lowering the frame rate by supplying a transmission signal for performing polarization processing within the non-diagnosis period.

The polarization processing can be performed in a period other than a period for acquiring an ultrasound image, that is, in a period before the first scanning line Line1 is scanned and after the last scanning line Line128 is scanned.

On the other hand, in a case where a non-diagnosis period is not provided within each frame time, a transmission signal for performing polarization processing may be supplied by lowering the frame rate intentionally within a range in which there is no influence on the image quality of the ultrasound image. This is because it is considered that it would be acceptable to lower the image quality of an image (part of a moving image) by temporarily lowering the frame rate rather than lowering the image quality of the entire image (entire moving image) by lowering the reception sensitivity of the ultrasound transducer 48.

Alternatively, it is also possible to generate a non-diagnosis period during which transmission of ultrasound waves and reception of reflected waves for performing ultrasound diagnosis are not performed, within each frame time during the execution period of ultrasound diagnosis, by reducing at least one of the line density, the number of lines, or the line interval of a plurality of scanning lines scanned by electronic sector scanning for performing ultrasound diagnosis and perform polarization processing while maintaining the frame rate within the generated non-diagnosis period.

Here, the line density indicates a ratio of the number of scanning lines scanned within one frame time to the total number of scanning lines within one frame time. The number of lines indicates the number of scanning lines scanned within one frame time among a plurality of scanning lines within one frame time. The line interval indicates an interval of time from the scanning of one scanning line among a plurality of scanning lines within one frame time to the scanning of the next scanning line.

Figure 15:
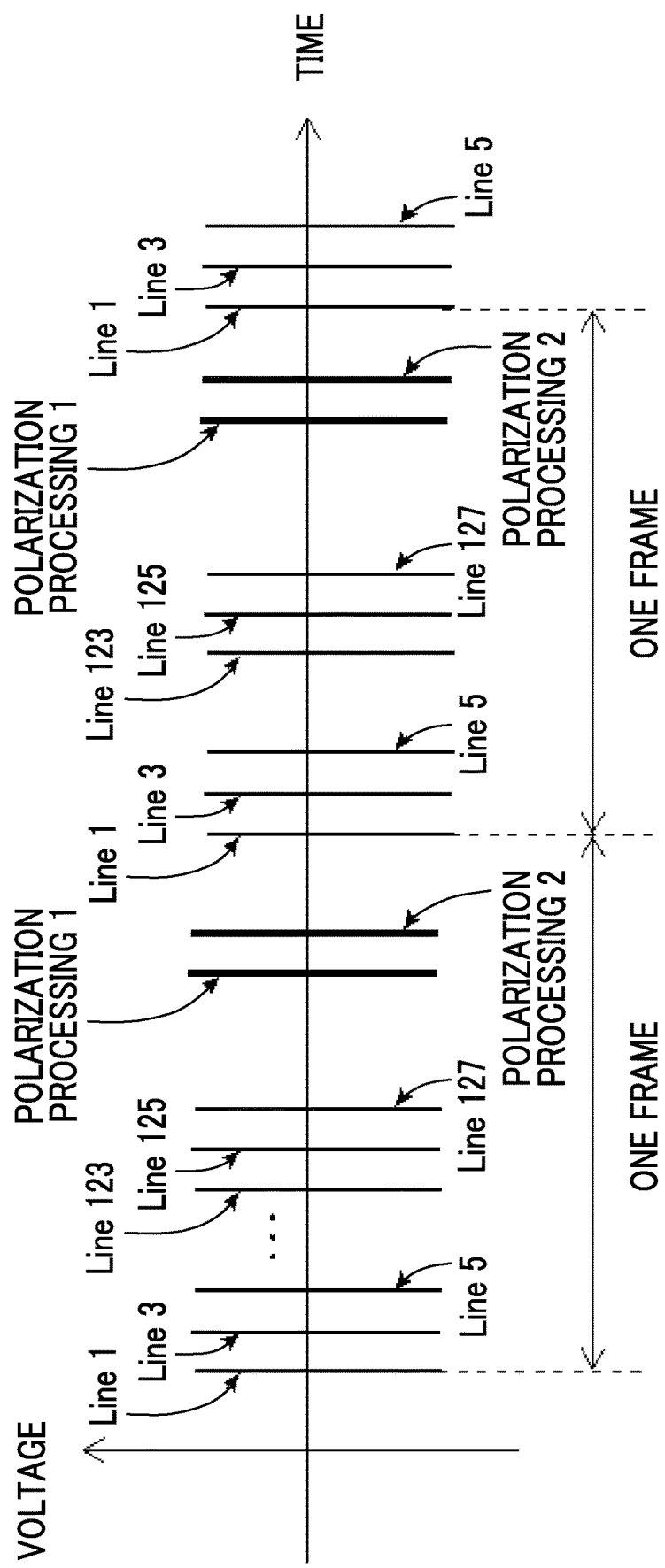
FIG. 15 is a conceptual diagram of an example showing the timing of supplying a transmission signal for performing polarization processing in a case where the line density of scanning lines for performing ultrasound diagnosis is reduced.

FIG. 15 is a conceptual diagram of an example showing the timing of supplying a transmission signal for performing polarization processing in a case where the line density of scanning lines for performing ultrasound diagnosis is reduced.

In this case, as shown in FIG. 15, within each frame time, scanning of the even-numbered 64 scanning lines Line2, Line4, . . . , and Line128 is omitted, and scanning of the odd-numbered 64 scanning lines Line1, Line3, . . . , and Line127 is sequentially performed. Then, within each frame time, after the end of the scanning of the last scanning line Line127, in a non-diagnosis period generated by omitting the scanning of the even-numbered 64 scanning lines Line2, Line4, . . . , and Line128, polarization processing is performed as in the case of FIG. 14.

In this manner, since a non-diagnosis period can be generated within each frame time by reducing the line density of scanning lines for performing ultrasound diagnosis, it is possible to perform the polarization processing within the generated non-diagnosis period while maintaining the frame rate.

The scanning of the odd-numbered 64 scanning lines Line1, Line3, . . . , and Line 127 may be omitted, and only the scanning of the even-numbered 64 scanning lines Line2, Line4, . . . , and Line 128 may be performed. In addition, the scanning of the next one or more scanning lines may be omitted each time one or more scanning lines are scanned. For example, the scanning of the next one scanning line is omitted each time two scanning lines are scanned. In the case of reducing the line density of the scanning lines, the rate of reducing the line density of the scanning lines can be appropriately determined according to the image quality of the ultrasound image, the time required to perform polarization processing, and the like.

Figure 16:
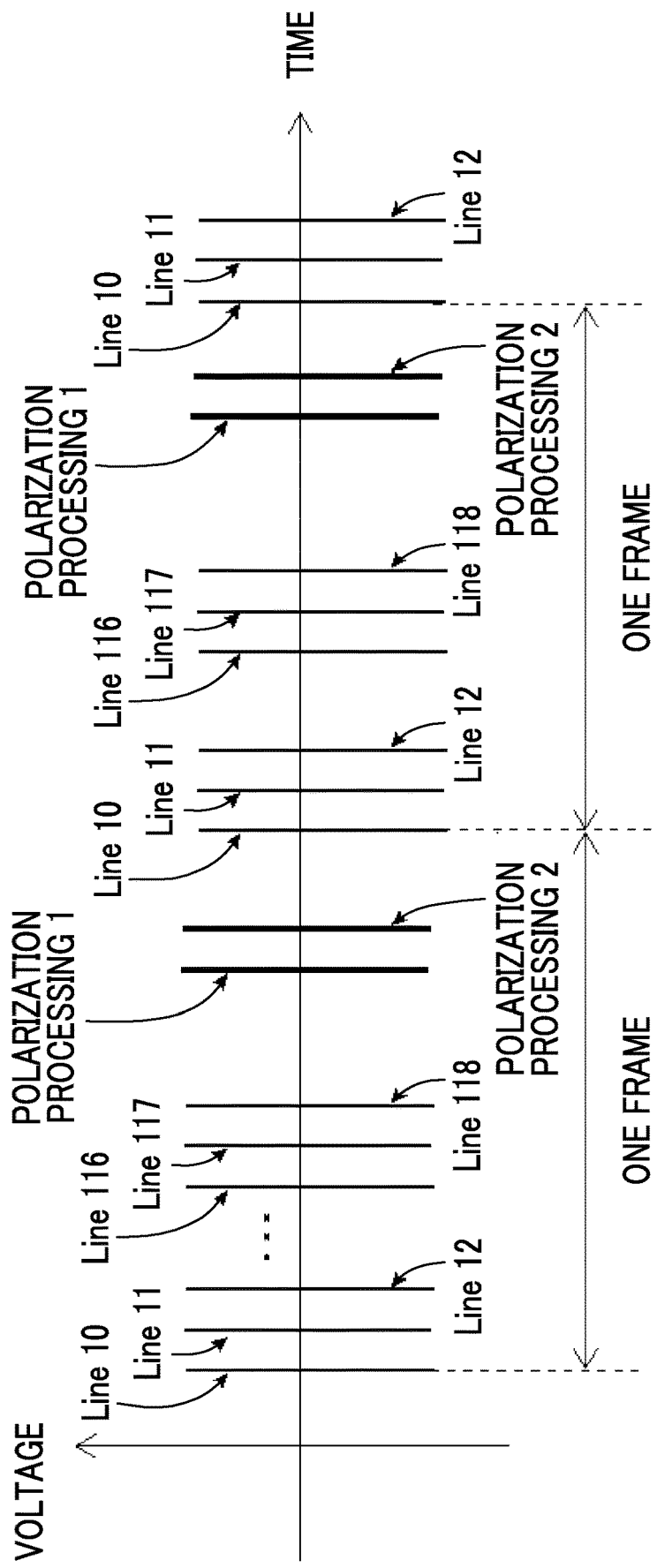
FIG. 16 is a conceptual diagram of an example showing the timing of supplying a transmission signal for performing polarization processing in a case where the number of scanning lines for performing ultrasound diagnosis is reduced.

Subsequently, FIG. 16 is a conceptual diagram of an example showing the timing of supplying a transmission signal for performing polarization processing in a case where the number of scanning lines for performing ultrasound diagnosis is reduced.

In this case, as shown in FIG. 16, within each frame time, scanning of the nine scanning lines Line1 to Line9 on the right end portion side and the ten scanning lines Line119 to Line128 on the left end portion side is omitted, and the scanning of the 109 scanning lines Line10 to Line118 at the central portion is sequentially performed. Then, within each frame time, after the end of the scanning of the last scanning line Line118, in a non-diagnosis period generated by omitting the scanning of the scanning lines Line1 to Line9 and the scanning lines Line119 to Line128, polarization processing is performed as in the case of FIG. 14.

In this manner, since a non-diagnosis period can be generated within each frame time by reducing the number of scanning lines for performing ultrasound diagnosis, it is possible to perform the polarization processing within the generated non-diagnosis period while maintaining the frame rate.

Within each frame time, it is not essential to omit the scanning of the scanning lines at both end portions, and only the scanning of the scanning line at one end portion may be omitted. In the case of reducing the number of scanning lines, the number of scanning lines to be reduced can be appropriately determined according to the time required to perform polarization processing and the like. In addition, in the case of reducing the number of scanning lines, it is preferable to omit scanning of scanning lines sequentially from the end portion side rather than omitting scanning of scanning lines at the central portion in order to prevent the image quality of the ultrasound image from lowering.

Figure 17:
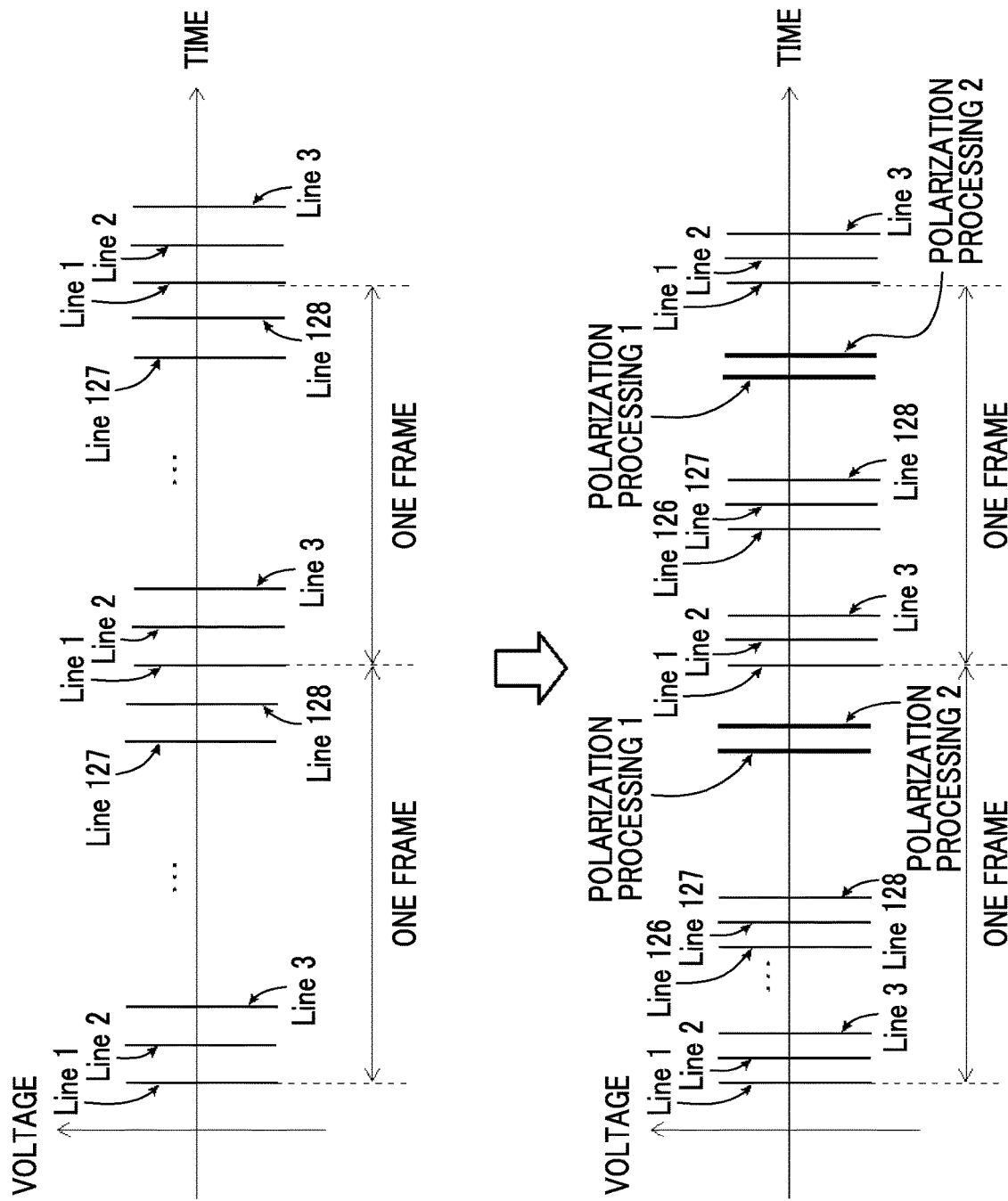
FIG. 17 is a conceptual diagram of an example showing the timing of supplying a transmission signal for performing polarization processing in a case where the line interval between scanning lines for performing ultrasound diagnosis is reduced.

Subsequently, FIG. 17 is a conceptual diagram of an example showing the timing of supplying a transmission signal for performing polarization processing in a case where the line interval of scanning lines for performing ultrasound diagnosis is reduced.

In this case, as shown from a state shown on the upper side to a state shown on the lower side in FIG. 17, within each frame time, the line interval between the scanning lines Line1 to Line128 (time interval between two adjacent scanning lines) is reduced (narrowed), and the scanning of the scanning lines Line1 to Line128 is sequentially performed. Then, within each frame time, after the end of the scanning of the last scanning line Line128, in a non-diagnosis period generated by reducing the line interval between the scanning lines Line1 to Line128, polarization processing is performed as in the case of FIG. 14.

The line interval between the scanning lines is generally determined according to the time from transmission of the ultrasound wave to reception of the reflected wave or the like. In a case where the line interval between the scanning lines is reduced too much, the acquired ultrasound image may be adversely affected. However, for the line interval between the scanning lines, a margin time is usually set in addition to the time from transmission of the ultrasound wave to reception of the reflected wave. Therefore, within the range of the margin time, it is possible to reduce the line interval between the scanning lines without lowering the image quality of the ultrasound image.

In this manner, since a non-diagnosis period can be generated within each frame time by reducing the line interval between the scanning lines for performing ultrasound diagnosis, it is possible to perform the polarization processing within the generated non-diagnosis period while maintaining the frame rate.

In the case of reducing the line interval between the scanning lines within each frame time, the time for which the line interval between the scanning lines is to be reduced can be appropriately determined according to the time required to perform the polarization processing and the like within the range in which the line interval between the scanning lines can be reduced.

In addition, in the case of performing ultrasound diagnosis, the number of times of driving of the ultrasound transducer 48 disposed at the central portion is larger than that on the end portion side. Therefore, the ultrasound transducer 48 disposed at the central portion has a higher risk of depolarization than that disposed on the end portion side.

In the case of the present embodiment, the number of opening channels is 64. Therefore, in the case of scanning the scanning line Line64 at the central portion, 64 ultrasound transducers 48 on both sides of the ultrasound transducer 48 at the central portion, for example, a total of 64 ultrasound transducers 48 including 32 ultrasound transducers 48 on the left end portion side from the ultrasound transducer 48 at the central portion and 32 ultrasound transducers 48 on the right end portion side from the ultrasound transducer 48 adjacent rightward to the ultrasound transducer 48 at the central portion are simultaneously driven. The same applies to the case of scanning the other scanning lines Line33 to Line96 at the central portion.

On the other hand, in the case of scanning the scanning line Line1 at the right end portion, since the number of opening channels is 64 but there is no ultrasound transducer 48 on the further right side of the ultrasound transducer 48 at the right end portion, only the 32 ultrasound transducers 48 on the central portion side from the ultrasound transducer 48 at the right end portion are simultaneously driven.

In the case of scanning the second scanning line from the right end, only one ultrasound transducer 48 at the right end portion is present on the right side of the second ultrasound transducer 48 from the right end. Therefore, a total of only 33 ultrasound transducers 48 including the 32 ultrasound transducers 48 on the central portion side from the second ultrasound transducer 48 from the right end and one ultrasound transducer 48 at the right end portion are simultaneously driven.

The same applies to the case of scanning the third to 32nd scanning lines Line3 to Line32 from the right end, and only a total of 34 to 63 ultrasound transducers 48 are simultaneously driven. In addition, the same applies to the case of scanning the scanning lines Line97 to Line128 on the left end portion side. Therefore, within each frame time, it is desirable to make the time for performing polarization processing on the ultrasound transducer 48 disposed at the central portion longer than the time for performing polarization processing on the ultrasound transducers 48 disposed at both end portions.

Next, the timing of supplying a transmission signal for making the time for performing polarization processing on the ultrasound transducer 48 disposed at the central portion longer than the time for performing polarization processing on the ultrasound transducers 48 disposed at both end portions in the case of performing the polarization processing during the execution period of ultrasound diagnosis will be described.

Figure 18:
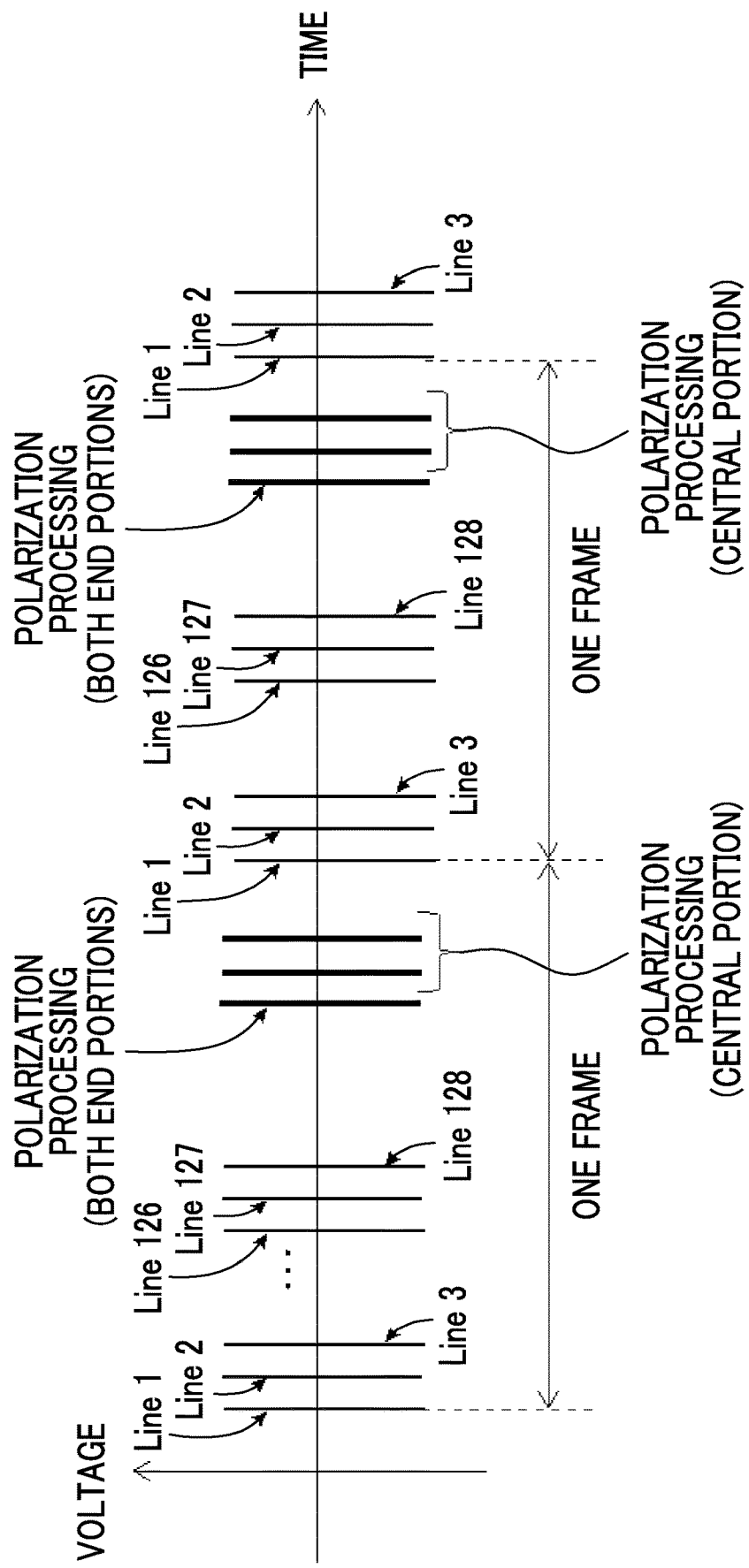
FIG. 18 is a conceptual diagram of an example showing the timing of supplying a transmission signal for making the time for performing polarization processing on the ultrasound transducer disposed at the central portion longer than the time for performing polarization processing on the ultrasound transducers disposed at both end portions in the case of performing the polarization processing during the execution period of ultrasound diagnosis.

FIG. 18 is a conceptual diagram of an example showing the timing of supplying a transmission signal for making the time for performing polarization processing on the ultrasound transducer 48 disposed at the central portion longer than the time for performing polarization processing on the ultrasound transducers 48 disposed at both end portions in the case of performing the polarization processing during the execution period of ultrasound diagnosis.

Figure 19:
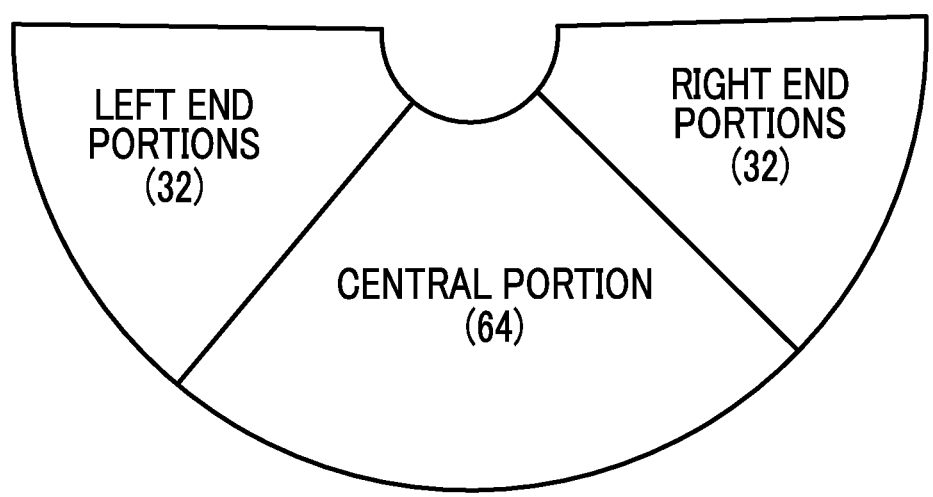
FIG. 19 is a conceptual diagram of an example showing ultrasound transducers at a central portion and ultrasound transducers at both end portions.

In this case, as shown in FIG. 18, within each frame time, scanning of the scanning lines Line1 to Line128 for performing ultrasound diagnosis is sequentially performed as in the case shown in FIG. 12. Then, in a non-diagnosis period after the end of scanning of the last scanning line Line128 within each frame time, as shown in FIG. 19, polarization processing on the 64 ultrasound transducers 48 in the central portion and polarization processing on the 64 ultrasound transducers 48 at both end portions including the 32 ultrasound transducers 48 at the right end portion and the 32 ultrasound transducers 48 at the left end portion are separately performed.

In the case of the present embodiment, three transmission signals called polarization processing 1 to 3 are supplied as transmission signals for performing polarization processing. A transmission signal of polarization processing 1 is supplied to a total of 64 ultrasound transducers 48 including the 32 ultrasound transducers 48 at the right end portion and the 32 ultrasound transducers 48 at the left end portion, among the 128 ultrasound transducers 48, and then transmission signals of polarization processing 2 and 3 are supplied to the 64 ultrasound transducers 48 at the central portion.

That is, within each frame time, the polarization processing is performed once on the 64 ultrasound transducers 48 at both end portions, while the polarization processing is performed twice on the 64 ultrasound transducers 48 at the central portion. As a result, with respect to the 64 ultrasound transducers 48 at the central portion having a higher risk of depolarization than the 64 ultrasound transducers 48 at both end portions, the polarization processing can be performed twice as long as the 64 ultrasound transducers 48 at both end portions.

In addition, the time for performing the polarization processing on the ultrasound transducers 48 disposed at the central portion may be made to be longer than that on the ultrasound transducers 48 disposed at both end portions. For example, the time of polarization processing performed on the 64 ultrasound transducers 48 at the central portion may be twice the time of polarization processing performed on the 64 ultrasound transducers 48 at both end portions or longer.

Next, a trigger generation timing, that is, a timing for starting polarization processing will be described.

Depolarization of the ultrasound transducer 48 progresses as dipoles applied to both sides of the ultrasound transducer 48 decrease according to the time for which transmission of ultrasound waves and reception of reflected waves for performing ultrasound diagnosis are performed, that is, according to the cumulative driving time of the plurality of ultrasound transducers 48.

The trigger generation circuit 156 cannot directly determine whether or not the ultrasound transducer 48 is depolarized. Accordingly, for example, the trigger generation circuit 156 can determine whether or not the ultrasound transducer 48 is depolarized based on the above-described cumulative driving time of the ultrasound transducers 48 and generate a trigger in a case where the cumulative driving time of the plurality of ultrasound transducers 48 for performing ultrasound diagnosis becomes equal to or longer a specified time.

As the specified time, a default value of the time may be set in the trigger generation circuit 156, or any time may be set according to the user's instruction. The specified time is any time, and may be on the order of several hours or on the order of several frame times.

The trigger generation circuit 156 can generate a trigger in a case where a button for giving an instruction to start polarization processing is pressed according to the user's instruction. That is, the polarization processing can be started at any timing according to the user's instruction.

The button may be an electronic button displayed within the touch panel of the console 100, or may be a mechanical button provided on the operation unit 24 of the ultrasound endoscope 12.

In addition, the trigger generation circuit 156 can generate a trigger in a case where the ultrasound image generation mode is set to the contrast mode in which a contrast image acquired using a contrast medium is highlighted. In the contrast mode, the ultrasound wave transmitted from the ultrasound transducer 48 is generally set to have a low output that does not destroy bubbles contained in the contrast medium. Therefore, since the S/N ratio of the image is reduced, an adverse effect of sensitivity lowering due to depolarization is likely to appear.

In a case where the depolarization of the ultrasound transducer 48 progresses and its reception sensitivity lowers, an ultrasound image acquired at a position where the display depth is relatively large is likely to have a lower S/N ratio than an ultrasound image acquired at a position where the display depth is relatively small, and the image quality is easily degraded. For this reason, the trigger generation circuit 156 can generate a trigger in a case where the display depth of the ultrasound image for performing ultrasound diagnosis is set to a predetermined depth or more.

The display depth of the ultrasound image for performing ultrasound diagnosis can be set to, for example, a position of 4 cm in depth and a position of 10 cm in depth according to the user's instruction. For example, assuming that the predetermined depth described above is set to 5 cm, the trigger generation circuit 156 does not generate a trigger in a case where the display depth of the ultrasound image is set to a position of 4 cm in depth, and generates a trigger in a case where the display depth of the ultrasound image is set to a position of 10 cm in depth.

As the predetermined depth, a default value of the depth may be set in the trigger generation circuit 156, or any depth may be set according to the user's instruction.

Similarly, in a case where the depolarization of the ultrasound transducer 48 progresses and its reception sensitivity lowers, a B mode ultrasound image acquired at a position where the display depth is relatively large is likely to have a lower brightness than a B mode ultrasound image acquired at a position where the display depth is relatively small. For this reason, the trigger generation circuit 156 can generate a trigger in a case where the brightness of the B mode ultrasound image, which is acquired in a state in which the display depth is set to a predetermined depth or more, is equal to or less than a predetermined brightness.

As the predetermined brightness, a default value of the brightness may be set in the trigger generation circuit 156, or any brightness may be set according to the user's instruction.

In addition, by analyzing the ultrasound image during the execution period of the ultrasound diagnosis, it is possible to recognize that the user is performing treatment while viewing the ultrasound image. For example, it is possible to recognize whether or not the user is in the process of insertion, whether or not the stent is being released, or whether or not 30 minutes has passed from the start of acquisition of the ultrasound image. In this case, during the treatment, an endoscope image and an X-ray fluoroscopic image are often used in combination. Accordingly, compared with a case where an ultrasound image is used as a main image, polarization processing can be appropriately performed regardless of the image quality since attention is not paid to details of the ultrasound image. For this reason, the trigger generation circuit 156 can generate a trigger in a case where it is recognized based on the ultrasound image that the user is performing treatment while viewing the ultrasound image.

The ultrasound diagnostic apparatus 10 can acquire an ultrasound image and an endoscope image and display the ultrasound image and the endoscope image on the monitor 20 in various display modes.

As shown in FIG. 20, the display modes include a first display mode in which only an ultrasound image is displayed, a second display mode in which an ultrasound image is displayed so as to be larger than an endoscope image by using picture in picture (PinP), a third display mode in which an ultrasound image is displayed so as to be smaller than an endoscope image by using the PinP similarly, and a fourth display mode in which only an endoscope image is displayed. The first to fourth display modes can be freely switched and displayed according to the user's instruction.

Here, in the third display mode, since the ultrasound image is displayed so as to be smaller than the endoscope image, it is possible to appropriately perform the polarization processing regardless of the image quality. For this reason, the trigger generation circuit 156 can generate a trigger in a case where the ultrasound image is displayed so as to be smaller than the endoscope image by the picture in picture in the third display mode.

Although the trigger generation factors have been exemplified, the trigger may be generated based on any factor other than the above-described factors.

As the end conditions of the polarization processing, for example, a case where the cumulative processing time of the polarization processing reaches a predetermined time, a case where the user gives an instruction to end the polarization processing, a case where the contrast mode is changed to another ultrasound image generation mode, a case where the display depth of the ultrasound wave for performing ultrasound diagnosis is set to be smaller than a predetermined depth, a case where it is not recognized whether or not the user is performing treatment based on the endoscope image, a case where the brightness of the B mode ultrasound image acquired at a position where the display depth of the ultrasound wave is relatively large becomes larger than a predetermined brightness, and a case where the third display mode is changed to another display mode can be considered. However, the polarization processing may be ended according to end conditions other than those described above.

<<Effectiveness of Ultrasound Diagnostic Apparatus 10 of the Invention>>

The ultrasound diagnostic apparatus 10 performs polarization processing in a non-diagnosis period, which is a period other than the acquisition period of an image of each frame and during which transmission of ultrasound waves and reception of reflected waves for performing ultrasound diagnosis are not performed, within each frame time during the execution period of ultrasound diagnosis. Therefore, even during the execution period of the ultrasound diagnosis, the frame rate is not reduced. As a result, since the reception sensitivities of the plurality of ultrasound transducers 48 can always be kept satisfactory without reducing the image quality of the ultrasound image, a high-quality ultrasound image can always be acquired.

In addition, since the ultrasound diagnostic apparatus 10 performs the polarization processing using the existing transmission circuit 144, more specifically, the pulse generation circuit 158, it is possible to perform the polarization processing during the execution period of the ultrasound diagnosis without significantly changing the existing circuit.

The total number of ultrasound transducers 48 and the number of opening channels may be changed to any number. For example, in a case where the number of opening channels is the same as the total number of ultrasound transducers 48, one transmission signal for polarization processing for driving the 128 ultrasound transducers 48 can also be supplied instead of the two transmission signals for polarization processing called the above-described polarization processing 1 and 2. Alternatively, in a case where the number of opening channels is ¼ of the total number of ultrasound transducers 48, four transmission signals for polarization processing called polarization processing 1 to 4 for driving the 32 ultrasound transducers 48 can also be supplied.

The polarization processing may be performed by combining the case of reducing the line density of scanning lines, the case of reducing the number of scanning lines, and the case of reducing the line interval of scanning lines. Alternatively, it is also possible to perform the polarization processing by combining the case of reducing at least one of the line density of scanning lines, the number of scanning lines, or the line interval of scanning lines and the case of making the time for performing the polarization processing on the ultrasound transducer 48 disposed at the central portion longer than the time for performing the polarization processing on the ultrasound transducers 48 disposed at both end portions. Other than the above, the characteristics of the above respective embodiments may be implemented in combination.

The transmission circuit 144 may generate the first transmission signal using the first pulse generation circuit 158 and generate the second transmission signal using the second pulse generation circuit. That is, the first transmission signal and the second transmission signal may be generated using different pulse generation circuits in the transmission circuit 144.

In the example described above, the non-diagnosis period during which transmission of ultrasound waves and reception of reflected waves for performing ultrasound diagnosis are not performed is a period other than the acquisition period of an image of each frame, within each frame time for which an image of each frame of an ultrasound image is acquired during the execution period of ultrasound diagnosis. However, the invention is not limited thereto.

In the invention, the non-diagnosis period during which polarization processing is performed on the plurality of ultrasound transducers 48 may be any time or any period or may be a time or a period other than the execution period of ultrasound diagnosis as long as transmission of ultrasound waves and reception of reflected waves for acquiring an ultrasound image are not performed. The polarization processing may be performed on the plurality of ultrasound transducers 48 in any non-diagnosis time or period during which acquisition of an ultrasound image and execution of ultrasound diagnosis are not performed.

In the example described above, after the trigger for starting the polarization processing is given from the trigger generation circuit 156, the polarization processing is performed in the non-diagnosis period during the execution period of the ultrasound diagnosis. However, the invention is not limited thereto. In the non-diagnosis time or period, the polarization processing may be performed automatically or manually forcibly at the same time as switching to the non-diagnosis time or period.

The invention may further provide an ultrasound diagnostic apparatus and an operation method of an ultrasound diagnostic apparatus capable of performing polarization processing during the execution period of ultrasound diagnosis without affecting the image quality of an ultrasound image.

In addition to the above object, the invention may further provide an ultrasound diagnostic apparatus and an operation method of an ultrasound diagnostic apparatus capable of performing polarization processing without significantly changing the existing circuit.

The ultrasound diagnostic apparatus of the invention is an ultrasound diagnostic apparatus that acquires an ultrasound image and an endoscope image, and comprises: an ultrasound endoscope comprising an ultrasound observation portion that transmits ultrasound waves using an ultrasound transducer array in which a plurality of ultrasound transducers are arranged, receives reflected waves of the ultrasound waves, and outputs a reception signal; and an ultrasound processor apparatus that generates an ultrasound image by converting the reception signal into an image. The ultrasound processor apparatus may comprises a trigger generation circuit that generates a trigger for starting polarization processing and a control circuit that performs the polarization processing on the plurality of ultrasound transducers in a non-diagnosis period, which is a period other than a period for acquiring an image of each frame and during which transmission of the ultrasound waves and reception of the reflected waves for performing ultrasound diagnosis are not performed, within each frame time in which an image of each frame of an ultrasound image is acquired during the execution period of the ultrasound diagnosis after the trigger is given.

Here, it is preferable that the ultrasound processor apparatus further comprises a transmission circuit that generates a transmission signal for driving the plurality of ultrasound transducers to generate ultrasound waves using a pulse generation circuit and supplies the transmission signal to the plurality of ultrasound transducers under the control of the control circuit. It is preferable that the transmission circuit generates a first transmission signal for performing ultrasound diagnosis using a pulse generation circuit in the case of performing the ultrasound diagnosis and generates a second transmission signal for performing polarization processing using the same pulse generation circuit as in the case of generating the first transmission signal in the case of performing the polarization processing.

It is preferable that the control circuit generates a non-diagnosis period by reducing the line density, which indicates the ratio of the number of scanning lines scanned within one frame time to the total number of a plurality of scanning lines scanned by electronic sector scanning for acquiring an image of one frame of an ultrasound image, and performs the polarization processing within the generated non-diagnosis period.

It is preferable that the control circuit generates a non-diagnosis period by reducing the number of lines indicating the number of scanning lines scanned within one frame time, among a plurality of scanning lines scanned by electronic sector scanning for acquiring an image of one frame of an ultrasound image, and performs the polarization processing within the generated non-diagnosis period.

It is preferable that the control circuit generates a non-diagnosis period by reducing the line interval, which indicates an interval of time from scanning of one scanning line among a plurality of scanning lines scanned by electronic sector scanning for acquiring an image of one frame of an ultrasound image to scanning of the next scanning line, and performs the polarization processing within the generated non-diagnosis period.

It is preferable that, during the ultrasound diagnosis, in a case where the number of ultrasound transducers driven simultaneously is less than the total number of the plurality of ultrasound transducers, the control circuit sets the time for performing polarization processing on ultrasound transducers disposed at a central portion to be longer than the time for performing polarization processing on ultrasound transducers disposed at both end portions within each frame time.

It is preferable that the trigger generation circuit generates a trigger in a case where the cumulative driving time of the plurality of ultrasound transducers for performing ultrasound diagnosis becomes equal to or greater than a specified time. It is preferable that the trigger generation circuit generates a trigger in a case where a button for giving an instruction to start polarization processing is pressed.

It is preferable that the trigger generation circuit generates a trigger in a case where the ultrasound image generation mode is set to a contrast mode in which a contrast image acquired using a contrast medium is highlighted.

It is preferable that the trigger generation circuit generates a trigger in a case where the display depth of an ultrasound image for performing ultrasound diagnosis is set to a predetermined depth or more.

It is preferable that the trigger generation circuit generates a trigger in a case where it is recognized based on the ultrasound image that the user is performing treatment while viewing the ultrasound image.

It is preferable that the trigger generation circuit generates a trigger in a case where the brightness of a B mode ultrasound image, which is acquired in a state in which the display depth is set to a predetermined depth or more, is equal to or less than a predetermined brightness.

It is preferable that the trigger generation circuit generates a trigger in a case where an ultrasound image is displayed so as to be smaller than an endoscope image by picture in picture.

In addition, the invention provides an operation method of an ultrasound diagnostic apparatus acquiring an ultrasound image and an endoscope image. The operation method of an ultrasound diagnostic apparatus includes: a step in which an ultrasound observation portion that an ultrasound endoscope of the ultrasound diagnostic apparatus comprises transmits ultrasound waves using an ultrasound transducer array in which a plurality of ultrasound transducers are arranged, receives reflected waves of the ultrasound waves, and outputs a reception signal; and a step in which an ultrasound processor apparatus of the ultrasound diagnostic apparatus generates an ultrasound image by converting the reception signal into an image. The step of generating an ultrasound image includes: a step in which a trigger generation circuit of the ultrasound processor apparatus generates a trigger for starting polarization processing; and a step in which a control circuit of the ultrasound processor apparatus performs the polarization processing on the plurality of ultrasound transducers in a non-diagnosis period, which is a period other than a period for acquiring an image of each frame and during which transmission of the ultrasound waves and reception of the reflected waves for performing ultrasound diagnosis are not performed, within each frame time in which an image of each frame of an ultrasound image is acquired during the execution period of the ultrasound diagnosis after the trigger is given.

Here, it is preferable that the step of generating an ultrasound image further includes a step in which a transmission circuit of the ultrasound processor apparatus generates a transmission signal for driving the plurality of ultrasound transducers to generate ultrasound waves using a pulse generation circuit and supplies the transmission signal to the plurality of ultrasound transducers under the control of the control circuit.

It is preferable that the step of generating a transmission signal includes a step of generating a first transmission signal for performing ultrasound diagnosis using a pulse generation circuit in the case of performing the ultrasound diagnosis and a step of generating a second transmission signal for performing polarization processing using the same pulse generation circuit as in the case of generating the first transmission signal in the case of performing the polarization processing.

It is preferable that, in the step of performing polarization processing, a non-diagnosis period is generated by reducing the line density, which indicates the ratio of the number of scanning lines scanned within one frame time to the total number of a plurality of scanning lines scanned by electronic sector scanning for acquiring an image of one frame of an ultrasound image, and the polarization processing is performed within the generated non-diagnosis period.

It is preferable that, in the step of performing polarization processing, a non-diagnosis period is generated by reducing the number of lines indicating the number of scanning lines scanned within one frame time, among a plurality of scanning lines scanned by electronic sector scanning for acquiring an image of one frame of an ultrasound image, and the polarization processing is performed within the generated non-diagnosis period.

It is preferable that, in the step of performing polarization processing, a non-diagnosis period is generated by reducing the line interval, which indicates an interval of time from scanning of one scanning line among a plurality of scanning lines scanned by electronic sector scanning for acquiring an image of one frame of an ultrasound image to scanning of the next scanning line, and the polarization processing is performed within the generated non-diagnosis period.

It is preferable that, in the step of performing polarization processing, during the ultrasound diagnosis, in a case where the number of ultrasound transducers driven simultaneously is less than the total number of the plurality of ultrasound transducers, the time for performing polarization processing on ultrasound transducers disposed at a central portion is set to be longer than the time for performing polarization processing on ultrasound transducers disposed at both end portions within each frame time.

According to the invention, polarization processing is performed in a non-diagnosis period, which is a period other than the acquisition period of an image of each frame and during which transmission of ultrasound waves and reception of reflected waves for performing ultrasound diagnosis are not performed, within each frame time during the execution period of ultrasound diagnosis. Therefore, even during the execution period of the ultrasound diagnosis, the frame rate is not reduced. As a result, since the reception sensitivities of the plurality of ultrasound transducers can always be kept satisfactory without reducing the image quality of the ultrasound image, a high-quality ultrasound image can always be acquired.

In addition, according to the invention, since the polarization processing is performed using the existing pulse generation circuit, it is possible to perform the polarization processing during the execution period of the ultrasound diagnosis without significantly changing the existing circuit.

While the invention has been described in detail, the invention is not limited to the above-described embodiments, and various improvements and modifications may be made without departing from the scope and spirit of the invention.

EXPLANATION OF REFERENCES

10: ultrasound diagnostic apparatus
12: ultrasound endoscope
14: ultrasound processor apparatus
16: endoscope processor apparatus
18: light source device
20: monitor
21a: water supply tank
21b: suction pump
22: insertion part
24: operation unit
26: universal cord
28a: air and water supply button
28b: suction button
29: angle knob
30: treatment tool insertion port
32a: ultrasound connector
32b: endoscope connector
32c: light source connector
34a: air and water supply tube
34b: suction tube
36: ultrasound observation portion
38: endoscope observation portion
40: distal end portion
42: bending portion
43: flexible portion
44: treatment tool lead-out port
45: treatment tool channel
46: ultrasound transducer unit
48: ultrasound transducer
50: ultrasound transducer array
54: backing material layer
56: coaxial cable
58: endoscope side memory
60: FPC
74: acoustic matching layer
76: acoustic lens
82: observation window
84: objective lens
86: solid-state imaging element
88: illumination window
90: cleaning nozzle
92: wiring cable
100: console
140: multiplexer
142: reception circuit
144: transmission circuit
146: A/D converter
148: ASIC
150: cine memory
151: memory controller
152: CPU
154: DSC
156: trigger generation circuit
158: pulse generation circuit
160: phase matching unit
162: B mode image generation unit
164: PW mode image generation unit
166: CF mode image generation unit

What is claimed is:

1. An operation method of an ultrasound diagnostic apparatus, comprising:
executing one or more imaging series of steps with a plurality of ultrasound transducers to acquire an ultrasound image to perform an ultrasound diagnosis; and
applying a polarization processing to the plurality of ultrasound transducers in a non-diagnostic period within each frame time during an execution period of the ultrasound diagnosis by executing the one or more imaging series of steps,
wherein the non-diagnostic period is a period other than a period for acquiring an image of each frame and during which transmission of ultrasound waves and reception of reflected waves for performing the ultrasound diagnosis are not performed, within the each frame time in which an image of each frame of the ultrasound image is acquired during the execution period of the ultrasound diagnosis, wherein, within one frame time in which an image of one frame is acquired by a plurality of scanning lines scanned by electronic sector scanning for performing the ultrasonic diagnosis using the plurality of ultrasonic transducers, the non-diagnostic period is a period from an end of scanning of a last scanning line of the plurality of scanning lines to a start of scanning of a first scanning line within a next one frame time, and wherein the polarization processing is separate from the one or more imaging series of steps.

2. The operation method of the ultrasound diagnostic apparatus according to claim 1, wherein executing the one or more imaging series of steps is executing one or more ultrasound image generation mode and includes sending an input signal adapted for imaging to the plurality of ultrasound transducers.

3. The operation method of the ultrasound diagnostic apparatus according to claim 2, wherein applying the polarization processing includes sending one or more polarization voltages adapted for repolarization of the plurality of ultrasound transducers to the plurality of ultrasound transducers, and wherein the polarization voltages are different than and separate from the input signal adapted for imaging.

4. The operation method of the ultrasound diagnostic apparatus according to claim 1, wherein applying the polarization processing is responsive to a received user's operation and occurs in the non-diagnostic period within the each frame time during the execution period of the ultrasound diagnosis by executing the one or more imaging series of steps.

5. The operation method of the ultrasound diagnostic apparatus according to claim 2, wherein applying the polarization processing is responsive to a received user's operation and occurs in the non-diagnostic period within the each frame time during the execution period of the ultrasound diagnosis by executing the one or more imaging series of steps.

6. The operation method of the ultrasound diagnostic apparatus according to claim 3, wherein applying the polarization processing is responsive to a received user's operation and occurs in the non-diagnostic period within the each frame time during the execution period of the ultrasound diagnosis by executing the one or more imaging series of steps.

7. The operation method of the ultrasound diagnostic apparatus according to claim 1, wherein applying the polarization processing occurs after a trigger generated in a case where it is recognized based on the ultrasound image that the user is performing treatment while viewing the ultrasound image is given while displaying the ultrasound image generated from echo signals received from executing the one or more imaging series of steps.

8. The operation method of the ultrasound diagnostic apparatus according to claim 2, wherein applying the polarization processing occurs after a trigger generated in a case where it is recognized based on the ultrasound image that the user is performing treatment while viewing the ultrasound image is given while displaying the ultrasound image generated from echo signals received from executing the one or more imaging series of steps.

9. The operation method of the ultrasound diagnostic apparatus according to claim 3, wherein applying the polarization processing occurs after a trigger generated in a case where it is recognized based on the ultrasound image that the user is performing treatment while viewing the ultrasound image is given while displaying the ultrasound image generated from echo signals received from executing the one or more imaging series of steps.

10. The operation method of the ultrasound diagnostic apparatus according to claim 4, wherein applying the polarization processing occurs after a trigger generated in a case where it is recognized based on the ultrasound image that the user is performing treatment while viewing the ultrasound image is given while displaying the ultrasound image generated from echo signals received from executing the one or more imaging series of steps.

11. The operation method of the ultrasound diagnostic apparatus according to claim 5, wherein applying the polarization processing occurs after a trigger generated in a case where it is recognized based on the ultrasound image that the user is performing treatment while viewing the ultrasound image is given while displaying the ultrasound image generated from echo signals received from executing the one or more imaging series of steps.

12. The operation method of the ultrasound diagnostic apparatus according to claim 6, wherein applying the polarization processing occurs after a trigger generated in a case where it is recognized based on the ultrasound image that the user is performing treatment while viewing the ultrasound image is given while displaying the ultrasound image generated from echo signals received from executing the one or more imaging series of steps.

13. The operation method of the ultrasound diagnostic apparatus according to claim 1, wherein the non-diagnostic period is generated within the each frame time during the execution period of ultrasound diagnosis, by reducing at least one of a line density, a number of lines, or a line interval of the plurality of scanning lines scanned by the electronic sector scanning.

14. An operation method of an ultrasound diagnostic apparatus, comprising:

executing one or more imaging series of steps with a plurality of ultrasound transducers to acquire an ultrasound image to perform an ultrasound diagnosis; and applying a polarization processing to the plurality of ultrasound transducers in a non-diagnostic period within each frame time during an execution period of the ultrasound diagnosis by executing the one or more imaging series of steps, wherein the non-diagnostic period is a period other than a period for acquiring an image of each frame and during which transmission of ultrasound waves and reception of reflected waves for performing the ultrasound diagnosis are not performed, within each frame time in which an image of each frame of the ultrasound image is acquired during the execution period of the ultrasound diagnosis, wherein, within one frame time in which an image of one frame is acquired by a plurality of scanning lines scanned by electronic sector scanning for performing the ultrasonic diagnosis using the plurality of ultrasonic transducers, the non-diagnostic period is a period from an end of scanning of a last scanning line of the plurality of scanning lines scanned within the one frame time to an end of the one frame time, and wherein the polarization processing is separate from the one or more imaging series of steps.

15. The operation method of the ultrasound diagnostic apparatus according to claim 14, wherein the non-diagnostic period is generated within the each frame time during the execution period of ultrasound diagnosis, by reducing at least one of a line density, a number of lines, or a line interval of the plurality of scanning lines scanned by the electronic sector scanning.

* * * * *